(12) United States Patent
Salahieh et al.

(10) Patent No.: US 8,287,584 B2
(45) Date of Patent: Oct. 16, 2012

(54) MEDICAL IMPLANT DEPLOYMENT TOOL

(75) Inventors: Amr Salahieh, Saratoga, CA (US);
Ulrich R. Haug, Campell, CA (US);
Claudio Argento, Los Gatos, CA (US);
Dwight Morejohn, Berkeley, CA (US);
Daniel Hildebrand, Menlo Park, CA
(US); Tom Saul, El Granada, CA (US)

(73) Assignee: Sadra Medical, Inc., Campbell, CA (US)

( * ) Notice: Subject to any disclaimer, the term of this patent is extended or adjusted under 35 U.S.C. 154(b) by 1656 days.

(21) Appl. No.: 11/274,889

(22) Filed: Nov. 14, 2005

(65) Prior Publication Data
US 2007/0112355 A1 May 17, 2007

(51) Int. Cl.
*A61F 2/06* (2006.01)
(52) U.S. Cl. ......... 623/1.11; 623/2.11; 606/108
(58) Field of Classification Search ........... 606/108;
623/1.11, 2.11, 2.2–2.26, 1.26, 1.32, 1.24,
623/2.1, 2.14, 2.17–2.18, 2.23–2.32, 1.15,
623/1.2, 2.4, 900
See application file for complete search history.

(56) References Cited

U.S. PATENT DOCUMENTS

| | | |
|---|---|---|
| 3,334,629 A | 8/1967 | Cohn |
| 3,409,013 A | 11/1968 | Berry |
| 3,540,431 A | 11/1970 | Mobin-Uddin |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,795,246 A | 3/1974 | Sturgeon |
| 3,839,741 A | 10/1974 | Haller |

(Continued)

FOREIGN PATENT DOCUMENTS
EP 0409929131 B1 4/1997
(Continued)

OTHER PUBLICATIONS

Andersen, H.R. et al. "Transluminal implantation of artificial heart valves. Description of a new expandable aortic valve and initial results with implantation by catheter technique in closed chest pigs." *Euro. Heart J.* 1992; 13:704-708.

(Continued)

*Primary Examiner* — Gary Jackson
*Assistant Examiner* — Erin Colello
(74) *Attorney, Agent, or Firm* — Seager, Tifte & Wickhem LLC

(57) ABSTRACT

A medical implant deployment tool and deployment method are disclosed. One aspect of the invention provides an implant system including an implant adapted for endovascular delivery and deployment; and a deployment tool adapted to deploy the implant, with the deployment tool having an actuation controller; a plurality of actuation elements adapted to apply forces to one or more implant deployment mechanisms and each adapted to extend along an actuation element path within a patient's vasculature; and an actuation element compensation mechanism adapted to compensate for differences in length between the actuation element paths. Another aspect of the invention provides a method of deploying an implant including the steps of endovascularly delivering an implant and implant deployment mechanisms to an implant site and applying an actuation force to the implant deployment mechanisms through actuation elements extending through the patient's vasculature while compensating for differences in length between actuation element path lengths to deploy the implant.

38 Claims, 19 Drawing Sheets

U.S. PATENT DOCUMENTS

| | | | |
|---|---|---|---|
| 3,868,956 A | 3/1975 | Alfidi et al. | |
| 3,874,388 A | 4/1975 | King et al. | |
| 4,056,854 A | 11/1977 | Boretos et al. | |
| 4,106,129 A | 8/1978 | Carpentier et al. | |
| 4,233,690 A | 11/1980 | Akins | |
| 4,291,420 A | 9/1981 | Reul | |
| 4,326,306 A | 4/1982 | Poler | |
| 4,423,809 A | 1/1984 | Mazzocco | |
| 4,425,908 A | 1/1984 | Simon | |
| 4,501,030 A | 2/1985 | Lane | |
| 4,580,568 A | 4/1986 | Gianturco | |
| 4,602,911 A | 7/1986 | Ahmadi et al. | |
| 4,610,688 A | 9/1986 | Silvestrini et al. | |
| 4,617,932 A | 10/1986 | Kornberg | |
| 4,647,283 A | 3/1987 | Carpentier et al. | |
| 4,648,881 A | 3/1987 | Carpentier et al. | |
| 4,655,218 A | 4/1987 | Kulik et al. | |
| 4,655,771 A | 4/1987 | Wallsten | |
| 4,662,885 A | 5/1987 | DiPisa, Jr. | |
| 4,665,906 A | 5/1987 | Jervis | |
| 4,710,192 A | 12/1987 | Liotta et al. | |
| 4,733,665 A | 3/1988 | Palmaz | |
| 4,755,181 A | 7/1988 | Igoe | |
| 4,796,629 A | 1/1989 | Grayzel | |
| 4,819,751 A | 4/1989 | Shimada et al. | |
| 4,834,755 A | 5/1989 | Silvestrini et al. | |
| 4,856,516 A | 8/1989 | Hillstead | |
| 4,865,600 A | 9/1989 | Carpentier et al. | |
| 4,872,874 A | 10/1989 | Taheri | |
| 4,909,252 A | 3/1990 | Goldberger | |
| 4,917,102 A | 4/1990 | Miller et al. | |
| 4,954,126 A | 9/1990 | Wallsten | |
| 4,986,830 A | 1/1991 | Owens et al. | |
| 4,994,077 A | 2/1991 | Dobben | |
| 5,002,556 A | 3/1991 | Ishida et al. | |
| 5,002,559 A | 3/1991 | Tower | |
| 5,064,435 A | 11/1991 | Porter | |
| 5,161,547 A | 11/1992 | Tower | |
| 5,163,953 A | 11/1992 | Vince | |
| 5,209,741 A | 5/1993 | Spaeth | |
| 5,217,483 A | 6/1993 | Tower | |
| 5,258,042 A | 11/1993 | Mehta | |
| 5,332,402 A | 7/1994 | Teitelbaum | |
| 5,336,258 A | 8/1994 | Quintero et al. | |
| 5,350,398 A | 9/1994 | Pavcnik et al. | |
| 5,370,685 A | 12/1994 | Stevens | |
| 5,389,106 A | 2/1995 | Tower | |
| 5,397,351 A | 3/1995 | Pavcnik et al. | |
| 5,411,552 A | 5/1995 | Andersen et al. | |
| 5,425,762 A | 6/1995 | Muller | |
| 5,431,676 A | 7/1995 | Dubrul et al. | |
| 5,443,495 A | 8/1995 | Buscemi et al. | |
| 5,443,499 A | 8/1995 | Schmitt | |
| 5,476,506 A | 12/1995 | Lunn | |
| 5,476,510 A | 12/1995 | Eberhardt et al. | |
| 5,480,423 A | 1/1996 | Ravenscroft et al. | |
| 5,507,767 A | 4/1996 | Maeda et al. | |
| 5,534,007 A * | 7/1996 | St. Germain et al. | 623/1.11 |
| 5,545,133 A | 8/1996 | Burns et al. | |
| 5,545,211 A | 8/1996 | An et al. | |
| 5,549,665 A | 8/1996 | Vesely et al. | |
| 5,554,185 A | 9/1996 | Block et al. | |
| 5,571,215 A | 11/1996 | Sterman et al. | |
| 5,575,818 A | 11/1996 | Pinchuk | |
| 5,626,553 A * | 5/1997 | Frassica et al. | 600/146 |
| 5,645,559 A | 7/1997 | Hachtman et al. | |
| 5,662,671 A | 9/1997 | Barbut et al. | |
| 5,667,523 A | 9/1997 | Bynon et al. | |
| 5,674,277 A | 10/1997 | Freitag | |
| 5,693,083 A | 12/1997 | Baker et al. | |
| 5,695,498 A | 12/1997 | Tower | |
| 5,713,953 A | 2/1998 | Vallana et al. | |
| 5,716,370 A | 2/1998 | Williamson, IV et al. | |
| 5,720,391 A | 2/1998 | Dohm et al. | |
| 5,733,325 A | 3/1998 | Robinson et al. | |
| 5,735,842 A * | 4/1998 | Krueger et al. | 606/1 |
| 5,769,812 A | 6/1998 | Stevens et al. | |
| 5,800,456 A | 9/1998 | Maeda et al. | |
| 5,807,405 A * | 9/1998 | Vanney et al. | 623/2.11 |
| 5,817,126 A | 10/1998 | Imran | |
| 5,824,041 A | 10/1998 | Lenker et al. | |
| 5,824,043 A | 10/1998 | Cottone, Jr. | |
| 5,824,053 A | 10/1998 | Khosravi et al. | |
| 5,824,055 A | 10/1998 | Spiridigliozzi et al. | |
| 5,824,056 A | 10/1998 | Rosenberg | |
| 5,824,064 A | 10/1998 | Taheri | |
| 5,840,081 A | 11/1998 | Andersen et al. | |
| 5,843,158 A | 12/1998 | Lenker et al. | |
| 5,855,597 A | 1/1999 | Jayaraman | |
| 5,855,601 A | 1/1999 | Bessler et al. | |
| 5,860,966 A | 1/1999 | Tower | |
| 5,860,996 A | 1/1999 | Tower | |
| 5,861,024 A * | 1/1999 | Rashidi | 607/122 |
| 5,861,028 A | 1/1999 | Angell | |
| 5,868,783 A | 2/1999 | Tower | |
| 5,876,448 A | 3/1999 | Thompson et al. | |
| 5,885,228 A | 3/1999 | Rosenman et al. | |
| 5,888,201 A | 3/1999 | Stinson et al. | |
| 5,891,191 A | 4/1999 | Stinson | |
| 5,895,399 A | 4/1999 | Barbut et al. | |
| 5,907,893 A | 6/1999 | Zadno-Azizi et al. | |
| 5,910,154 A | 6/1999 | Tsugita et al. | |
| 5,911,734 A | 6/1999 | Tsugita et al. | |
| 5,925,063 A | 7/1999 | Khosravi | |
| 5,944,738 A | 8/1999 | Amplatz et al. | |
| 5,954,766 A | 9/1999 | Zadno-Azizi et al. | |
| 5,957,949 A | 9/1999 | Leonhardt et al. | |
| 5,968,070 A | 10/1999 | Bley et al. | |
| 5,984,957 A | 11/1999 | Laptewicz, Jr. et al. | |
| 5,984,959 A | 11/1999 | Robertson et al. | |
| 5,993,469 A | 11/1999 | McKenzie et al. | |
| 5,997,557 A | 12/1999 | Barbut et al. | |
| 6,010,522 A | 1/2000 | Barbut et al. | |
| 6,022,370 A | 2/2000 | Tower | |
| 6,027,520 A | 2/2000 | Tsugita et al. | |
| 6,027,525 A | 2/2000 | Suh et al. | |
| 6,042,598 A | 3/2000 | Tsugita et al. | |
| 6,042,607 A | 3/2000 | Williamson, IV et al. | |
| 6,051,104 A | 4/2000 | Oriaran et al. | |
| 6,123,723 A | 9/2000 | Konya et al. | |
| 6,142,987 A | 11/2000 | Tsugita | |
| 6,143,987 A | 11/2000 | Tsugita | |
| 6,146,366 A | 11/2000 | Schachar | |
| 6,162,245 A | 12/2000 | Jayaraman | |
| 6,165,200 A | 12/2000 | Tsugita et al. | |
| 6,165,209 A | 12/2000 | Patterson et al. | |
| 6,168,579 B1 | 1/2001 | Tsugita | |
| 6,168,614 B1 | 1/2001 | Andersen et al. | |
| 6,171,327 B1 | 1/2001 | Daniel et al. | |
| 6,179,859 B1 | 1/2001 | Bates | |
| 6,187,016 B1 | 2/2001 | Hedges et al. | |
| 6,197,053 B1 | 3/2001 | Cosgrove et al. | |
| 6,200,336 B1 | 3/2001 | Pavcnik et al. | |
| 6,214,036 B1 | 4/2001 | Letendre et al. | |
| 6,221,006 B1 | 4/2001 | Dubrul et al. | |
| 6,221,091 B1 | 4/2001 | Khosravi | |
| 6,221,096 B1 * | 4/2001 | Aiba et al. | 623/1.11 |
| 6,231,544 B1 | 5/2001 | Tsugita et al. | |
| 6,231,551 B1 | 5/2001 | Barbut | |
| 6,241,757 B1 | 6/2001 | An et al. | |
| 6,245,102 B1 | 6/2001 | Jayaraman | |
| 6,251,135 B1 | 6/2001 | Stinson et al. | |
| 6,258,114 B1 | 7/2001 | Konya et al. | |
| 6,258,115 B1 | 7/2001 | Dubrul | |
| 6,258,120 B1 | 7/2001 | McKenzie et al. | |
| 6,267,783 B1 | 7/2001 | Letendre et al. | |
| 6,270,513 B1 | 8/2001 | Tsugita et al. | |
| 6,277,555 B1 | 8/2001 | Duran et al. | |
| 6,309,417 B1 | 10/2001 | Spence et al. | |
| 6,319,281 B1 | 11/2001 | Patel | |
| 6,327,772 B1 | 12/2001 | Zadno-Azizi et al. | |
| 6,336,934 B1 | 1/2002 | Gilson et al. | |
| 6,336,937 B1 | 1/2002 | Vonesh et al. | |
| 6,338,735 B1 | 1/2002 | Stevens | |
| 6,348,063 B1 | 2/2002 | Yassour et al. | |
| 6,352,708 B1 | 3/2002 | Duran et al. | |
| 6,361,545 B1 | 3/2002 | Macoviak et al. | |

| | | |
|---|---|---|
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,416,510 B1 * | 7/2002 | Altman et al. ............... 606/41 |
| 6,425,916 B1 * | 7/2002 | Garrison et al. ............ 623/2.11 |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,502 B2 | 11/2002 | Spence et al. |
| 6,494,909 B2 | 12/2002 | Greenhalgh |
| 6,503,272 B2 * | 1/2003 | Duerig et al. ............... 623/1.24 |
| 6,508,833 B2 | 1/2003 | Pavcnik |
| 6,527,800 B1 | 3/2003 | McGuckin, Jr. et al. |
| 6,530,949 B2 | 3/2003 | Konya et al. |
| 6,530,952 B2 * | 3/2003 | Vesely ........................ 623/2.18 |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 * | 12/2003 | DuBois et al. ............ 604/95.04 |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 * | 1/2004 | Mercereau et al. ........... 606/127 |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,730,118 B2 | 5/2004 | Spenser et al. |
| 6,730,377 B2 | 5/2004 | Wang |
| 6,733,525 B2 * | 5/2004 | Yang et al. ................... 623/2.18 |
| 6,736,846 B2 | 5/2004 | Cox |
| 6,752,828 B2 | 6/2004 | Thornton |
| 6,758,855 B2 | 7/2004 | Fulton, III et al. |
| 6,764,503 B1 * | 7/2004 | Ishimaru .................... 623/1.11 |
| 6,764,509 B2 | 7/2004 | Chinn et al. |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Hyodoh et al. |
| 6,814,746 B2 | 11/2004 | Thompson et al. |
| 6,821,297 B2 | 11/2004 | Snyders |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,872,226 B2 | 3/2005 | Cali |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,365 B1 * | 9/2005 | Fogarty et al. ................ 606/227 |
| 6,953,332 B1 | 10/2005 | Kurk et al. |
| 6,964,673 B2 | 11/2005 | Tsugita et al. |
| 6,969,395 B2 | 11/2005 | Eskuri |
| 6,974,464 B2 | 12/2005 | Quijano et al. |
| 6,974,474 B2 | 12/2005 | Pavenik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,122,020 B2 * | 10/2006 | Mogul ....................... 604/95.04 |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 * | 3/2007 | Gielen et al. ................. 607/129 |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,329,279 B2 * | 2/2008 | Haug et al. ................... 623/2.11 |
| 7,374,560 B2 | 5/2008 | Ressemann et al. |
| 7,445,631 B2 * | 11/2008 | Salahieh et al. ............. 623/2.18 |
| 7,632,298 B2 * | 12/2009 | Hijlkema et al. ............ 623/1.12 |
| 7,717,955 B2 * | 5/2010 | Lane et al. ................... 623/2.41 |
| 7,722,666 B2 * | 5/2010 | Lafontaine .................. 623/2.11 |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032481 A1 | 3/2002 | Gabbay |
| 2002/0055769 A1 | 5/2002 | Wang |
| 2002/0058995 A1 | 5/2002 | Stevens |
| 2002/0065485 A1 * | 5/2002 | DuBois et al. ............ 604/95.04 |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0151970 A1 * | 10/2002 | Garrison et al. ............. 623/2.11 |
| 2002/0161392 A1 | 10/2002 | Dubrul |
| 2002/0161394 A1 | 10/2002 | Macoviak et al. |
| 2002/0177766 A1 * | 11/2002 | Mogul ......................... 600/374 |
| 2002/0177772 A1 * | 11/2002 | Altman et al. ................ 600/431 |
| 2002/0188341 A1 | 12/2002 | Elliott |
| 2002/0188344 A1 | 12/2002 | Bolea et al. |
| 2003/0023303 A1 | 1/2003 | Palmaz et al. |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0050694 A1 | 3/2003 | Yang et al. |
| 2003/0055495 A1 | 3/2003 | Pease et al. |
| 2003/0060844 A1 | 3/2003 | Borillo et al. |
| 2003/0070944 A1 | 4/2003 | Nigam |
| 2003/0109924 A1 | 6/2003 | Cribier |
| 2003/0109930 A1 * | 6/2003 | Bluni et al. ................... 623/23.7 |
| 2003/0114912 A1 * | 6/2003 | Sequin et al. ................ 623/1.11 |

| Publication No. | Date | Inventor |
|---|---|---|
| 2003/0125795 A1 | 7/2003 | Pavcnik et al. |
| 2003/0130729 A1 | 7/2003 | Paniagua et al. |
| 2003/0135257 A1* | 7/2003 | Taheri ............... 623/1.11 |
| 2003/0144732 A1* | 7/2003 | Cosgrove et al. ........... 623/2.11 |
| 2003/0149476 A1 | 8/2003 | Damm et al. |
| 2003/0149478 A1 | 8/2003 | Figulla et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1* | 12/2003 | Derus et al. ............... 623/1.11 |
| 2003/0229390 A1 | 12/2003 | Ashton et al. |
| 2003/0233117 A1 | 12/2003 | Adams et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0088045 A1 | 5/2004 | Cox |
| 2004/0093016 A1 | 5/2004 | Root et al. |
| 2004/0098022 A1 | 5/2004 | Barone |
| 2004/0098099 A1 | 5/2004 | McCullagh et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1* | 6/2004 | Fogarty et al. ............... 623/2.37 |
| 2004/0127847 A1* | 7/2004 | DuBois et al. ............ 604/95.04 |
| 2004/0127979 A1 | 7/2004 | Wilson et al. |
| 2004/0133274 A1* | 7/2004 | Webler et al. ............ 623/2.11 |
| 2004/0138694 A1 | 7/2004 | Tran et al. |
| 2004/0138742 A1 | 7/2004 | Myers et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0181140 A1* | 9/2004 | Falwell et al. ............ 600/374 |
| 2004/0186563 A1 | 9/2004 | Lobbi |
| 2004/0204755 A1 | 10/2004 | Robin |
| 2004/0215331 A1 | 10/2004 | Chew et al. |
| 2004/0215339 A1 | 10/2004 | Drasler et al. |
| 2004/0220655 A1* | 11/2004 | Swanson et al. ............. 623/1.11 |
| 2004/0225321 A1 | 11/2004 | Krolik et al. |
| 2004/0254636 A1 | 12/2004 | Flagle et al. |
| 2005/0033402 A1 | 2/2005 | Cully et al. |
| 2005/0043711 A1 | 2/2005 | Corcoran et al. |
| 2005/0075662 A1 | 4/2005 | Pedersen et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1* | 5/2005 | Hojeibane et al. ........... 623/1.24 |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1* | 6/2005 | Haug et al. ............... 623/2.11 |
| 2005/0137693 A1* | 6/2005 | Haug et al. ............... 623/2.11 |
| 2005/0137694 A1* | 6/2005 | Haug et al. ............... 623/2.11 |
| 2005/0137695 A1 | 6/2005 | Salahieh et al. |
| 2005/0137696 A1 | 6/2005 | Salahieh et al. |
| 2005/0137697 A1* | 6/2005 | Salahieh et al. ............. 623/2.11 |
| 2005/0137698 A1* | 6/2005 | Salahieh et al. ............. 623/2.11 |
| 2005/0137699 A1* | 6/2005 | Salahieh et al. ............. 623/2.11 |
| 2005/0137701 A1 | 6/2005 | Salahieh et al. |
| 2005/0137702 A1* | 6/2005 | Haug et al. ............... 623/2.38 |
| 2005/0143809 A1* | 6/2005 | Salahieh et al. ............. 623/2.11 |
| 2005/0165352 A1 | 7/2005 | Henry et al. |
| 2005/0165477 A1 | 7/2005 | Anduiza et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0251252 A1* | 11/2005 | Stobie ............... 623/2.11 |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2005/0288627 A1* | 12/2005 | Mogul ............... 604/95.04 |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1* | 3/2006 | Salahieh et al. ............. 623/2.18 |
| 2006/0155312 A1 | 7/2006 | Levine et al. |
| 2006/0161249 A1 | 7/2006 | Realyvasquez et al. |
| 2006/0173524 A1* | 8/2006 | Salahieh et al. ............. 623/1.11 |
| 2006/0195183 A1 | 8/2006 | Navia et al. |
| 2006/0195186 A1* | 8/2006 | Drews et al. ............... 623/2.38 |
| 2006/0217802 A1* | 9/2006 | Ruiz et al. ............... 623/2.11 |
| 2006/0253191 A1* | 11/2006 | Salahieh et al. ............. 623/2.11 |
| 2006/0259134 A1 | 11/2006 | Schwammenthal et al. |
| 2006/0271166 A1 | 11/2006 | Thill et al. |
| 2007/0010877 A1* | 1/2007 | Salahieh et al. ............. 623/2.11 |
| 2007/0016286 A1 | 1/2007 | Herrmann et al. |
| 2007/0016288 A1* | 1/2007 | Gurskis et al. ............... 623/2.11 |
| 2007/0055340 A1* | 3/2007 | Pryor ............... 623/1.11 |
| 2007/0118214 A1* | 5/2007 | Salahieh et al. ............. 623/2.22 |
| 2007/0162107 A1* | 7/2007 | Haug et al. ............... 623/1.26 |
| 2007/0203503 A1* | 8/2007 | Salahieh et al. ............. 606/108 |
| 2008/0125859 A1* | 5/2008 | Salahieh et al. ............. 623/2.11 |
| 2008/0188928 A1* | 8/2008 | Salahieh et al. ............. 623/2.11 |
| 2008/0288054 A1 | 11/2008 | Pulnev et al. |
| 2009/0005863 A1 | 1/2009 | Goetz et al. |
| 2009/0222076 A1 | 9/2009 | Figulla et al. |
| 2009/0264759 A1* | 10/2009 | Byrd ............... 600/445 |

FOREIGN PATENT DOCUMENTS

| | | |
|---|---|---|
| EP | 1000590 A1 | 5/2000 |
| EP | 1057459 | 12/2000 |
| EP | 1057460 | 12/2000 |
| EP | 0937439 B1 | 9/2003 |
| EP | 1340473 | 9/2003 |
| EP | 1356793 | 10/2003 |
| EP | 1042045 B1 | 5/2004 |
| EP | 0819013 | 6/2004 |
| EP | 1589902 | 8/2004 |
| EP | 1605871 | 9/2004 |
| EP | 1229864 B1 | 4/2005 |
| EP | 1582178 A2 | 5/2005 |
| EP | 1430853 A3 | 6/2005 |
| EP | 1059894 B1 | 7/2005 |
| EP | 1551274 A2 | 7/2005 |
| EP | 1551336 A1 | 7/2005 |
| EP | 1562515 A1 | 7/2005 |
| EP | 1078610 B1 | 8/2005 |
| EP | 1576937 A2 | 9/2005 |
| EP | 1582179 A2 | 10/2005 |
| EP | 1469797 | 11/2005 |
| EP | 1600121 A1 | 11/2005 |
| EP | 1156757 B1 | 12/2005 |
| EP | 1616531 | 1/2006 |

| | | |
|---|---|---|
| WO | WO 93/15693 | 8/1993 |
| WO | WO 95/04556 | 2/1995 |
| WO | WO 95/29640 | 11/1995 |
| WO | WO 96/14032 | 5/1996 |
| WO | WO 96/24306 A1 | 8/1996 |
| WO | WO 98/36790 | 8/1998 |
| WO | WO 98/50103 A1 | 11/1998 |
| WO | WO 98/57599 A2 | 12/1998 |
| WO | WO 99/44542 A2 | 9/1999 |
| WO | WO 00/09059 | 2/2000 |
| WO | WO 00/44308 | 8/2000 |
| WO | WO 00/44313 | 8/2000 |
| WO | WO 00/49970 A1 | 8/2000 |
| WO | WO 00/67661 | 11/2000 |
| WO | WO 01/05331 | 1/2001 |
| WO | WO 01/08596 A1 | 2/2001 |
| WO | WO 01/10320 A1 | 2/2001 |
| WO | WO 01/10343 A1 | 2/2001 |
| WO | WO 01/35870 | 5/2001 |
| WO | WO 01/64137 | 9/2001 |
| WO | WO 02/36048 | 5/2002 |
| WO | WO 02/41789 A2 | 5/2002 |
| WO | WO 02/100297 | 12/2002 |
| WO | WO 03/003943 | 1/2003 |
| WO | WO 03/003949 | 1/2003 |
| WO | WO 03/011195 | 2/2003 |
| WO | WO03/030776 A2 | 4/2003 |
| WO | WO 03/015851 | 11/2003 |
| WO | WO03/094797 | 11/2003 |
| WO | WO 2004/019811 | 3/2004 |
| WO | WO 2004/023980 | 3/2004 |
| WO | WO 2004/041126 | 5/2004 |
| WO | WO 2004/047681 | 6/2004 |
| WO | WO 2005/062980 A2 | 7/2005 |
| WO | WO 2005/084595 A1 | 9/2005 |
| WO | WO 2005/087140 A1 | 9/2005 |

OTHER PUBLICATIONS

Atwood, A. et al. "Insertion of Heart Valves by Catheterization." Project Supervised by Prof. S. Muftu of Northeaster University 2001-2002: 36-40.

Bodnar, E. et al. Replacement Cardiac Valves—Chapter 13: Extinct cardiac valve prostheses. *Pergamon Publishing Corporation*. New York, 1991: 307-332.

Boudjemline, Y. et al. "Percutaneious implantation of a biological valve in the aorta to treat aortic valve insufficiency—a sheep study." *Med Sci. Monit*. 2002; vol. 8, No. 4: BR113-116.

Boudjemline, Y. et al. "Percutaneous implantation of a valve in the descending aorta in lambs." *Euro. Heart J*. 2002; 23: 1045-1049.

Boudjemline, Y. et al. "Percutaneous pulmonary valve replacement in a large right ventricular outflow tract: an experimental study." *Journal of the Americal College of Cardiology*. 2004; vol. 43(6): 1082-1087.

Boudjemline, Y. et al. "Percutaneous valve insertion: A new approach?" *J. of Thoracic and Cardio. Surg*. 2003; 125(3): 741-743.

Boudjemline, Y. et al. "Steps Toward Percutaneous Aortic Valve Replacement." *Circulation*. 2002; 105: 775-778.

Cribier, A. et al. "Early Experience with Percutaneous Transcatheter Implantation of Heart Valve Prosthesis for the Treatment of End-Stage Inoperable Patients with Calcific Aortic Stenosis." *J. of Am. Coll. of Cardio*. 2004; 43(4): 698-703.

Cribier, A., et al. "Percutaneous Transcatheter Implantation of an Aortic Valve Prosthesis for Calcific Aortic Stenosis: First Human Case Description." *Circulation*. 2002; 106: 3006-3008.

Cribier, A., et al. "Percutaneous Transcatheter Implantation of an Aortic Valve Prosthesis for Calcific Aortic Stenosis: First Human Case." *Percutaneous Valve Technologies, Inc*. 2002: 16 pages.

Ferrari, M. et al. "Percutaneous transvascular aortic valve replacement with self expanding stent-valve device." Poster from the presentation given at SMIT 2000, 12th International Conference. Sep. 5, 2000.

Hijazi, Z.M. "Transcatheter Valve Replacement: A New Era of Percutaneous Cardiac Intervention Begins." *J. of Am. College of Cardio*. 2004; 43(6): 1088-1089.

Huber, C.H. et al. "Do valved stents compromise coronary flow?" *European Jouranl of Cardio-thoracic Surgery*. 2004; vol. 25: 754-759.

Knudsen, L. L. et al. "Catheter-implanted prosthetic heart valves." *Int'l J. of Art. Organs*. 1993; 16(5): 253-262.

Kort, S. et al. "Minimally invasive aortic valve replacement: Echocardiographic and clinical results." *Am. Heart J*. 2001; 142(3): 476-481.

Love, C. et al. "The Autogenous Tissue Heart Valve: Current Status." *Journal of Caridac Surgery*. 1991; 6(4): 499-507.

Lutter, G. et al. "Percutaneous aortic valve replacement: An experimental study. I. Studies on implantation." *J. of Thoracic and Cardio. Surg*. 2002; 123(4): 768-776.

Moulopoulos, S. D. et al. "Catheter-Mounted Aortic Valves." *Annals of Thoracic Surg*. 1971; 11(5): 423-430.

Paniagua, D. et al. "Percutaneous heart valve in the chronic in vitro testing model." *Circulation*. 2002; 106: e51-e52.

Paniagua, D. et al. Heart Watch (2004). *Texas Heart Institute*. Spring, 2004 Edition: 8 pages.

Pavcnik, D. et al. "Percutaneous bioprosthetic venous valve: A long-term study in sheep." *J. of Vascular Surg*. 2002; 35(3): 598-603.

Phillips, S. J. at al. "A Temporary Cathetei-Tip Aortic Valve: Hemodynamic Effects on Experimental Acute Aortic Insufficiency." *Annals of Thoracic Surg*. 1976; 21(2): 134-136.

Sochman, J. et al. "Percutaneous Transcatheter Aortic Disc Valve Prosthesis Implantation: A Feasibility Study." *Cardiovasc. Intervent. Radiol*. 2000; 23: 384-388.

Stuart, M. "In Heart Valves, A Brave, New Non-Surgical World." *Start-Up*. 2004: 9-17.

Vahanian, A. et al. "Percutaneous Approaches to Valvular Disease." *Circulation*. 2004; 109: 1572-1579.

Van Herwerden, L. A. et al., "Percutaneous valve implantation: back to the future?" *Euro. Heart J*. 2002; 23(18): 1415-1416.

Zhou, J. Q. et al. "Self-expandable valved stent of large size: off-bypass implantation in pulmonary position." *Eur. J. Cardiothorac*. 2003; 24: 212-216.

Fawzi, et al., U.S. Appl. No. 11/155,309, entitled "Apparatus and methods for intravascular embolic protection," filed Jun. 16, 2005.

Salahieh, et al., U.S. Appl. No. 11/232,441, entitled "Methods and apparatus for endovascular heart valve replacement comprising tissue grasping elements," filed Sep. 20, 2005.

Salahieh, et al., U.S. Appl. No. 11/232,444, entitled "Methods and apparatus for endovascular heart valve replacement comprising tissue grasping elements," filed Sep. 20, 2005.

Salahieh, et al., U.S. Appl. No. 12/264,082 entitled "Repositionable heart valve and method," filed Nov. 3, 2008.

Salahieh, et al., U.S. Appl. No. 12/269,213 entitled "Everting heart valve," filed Nov. 12, 2008.

Salahieh, et al., U.S. Appl. No. 11/531,980, "Externally expandable heart valve anchor and method," filed Sep. 14, 2006.

Salahieh, et al., U.S. Appl. No. 11/532,019, "Methods and apparatus for endovascularly replacing heart valve," filed Sep. 14, 2006.

Salahieh, et al., U.S. Appl. No. 11/314,183, entitled "Medical Device Delivery," filed Dec. 20, 2005.

Salahieh, et al., U.S. Appl. No. 11/314,969, entitled "Methods and Apparatus for Performing Valvuloplasty," filed Dec. 20, 2005.

Haug, et al; U.S. Appl. No. 11/716,123, entitled "Methods and apparatus for endovascularly replacing a heart valve," filed Mar. 9, 2007.

Salahieh, et al; U.S. Appl. No. 11/706,549, entitled "Systems and Methods for Delivering a Medical Implant," filed Feb. 14, 2007.

Salahieh, et al; U.S. Appl. No. 11/732,906 entitled "Assessing the location and performance of replacement heart valves," filed Apr. 4, 2007.

Haug et al.; U.S. Appl. No. 12/028,452 entitled "Methods and apparatus for endovascularly replacing a patient's heart valve," filed Feb. 8, 2008.

Salahieh, et al., U.S. Appl. No. 11/275,912, entitled "Medical Implant Delivery and Deployment Tool," filed Feb. 2, 2006.

Salahieh, et al., U.S. Appl. No. 11/275,913, entitled "Two-Part Package for Medical Implant," filed Feb. 2, 2006.

Salahieh, et al., U.S. Appl. No. 12/132,304 entitled "Low profile heart valve and delivery system," filed Jun. 3, 2008.

Haug et al.; U.S. Appl. No. 12/492,512 entitled "Everting Heart Valve," filed Jun. 26, 2009.

Paul et al.; U.S. Appl. No. 12/578,463 entitled "Medical Devices and Delivery Systems for Delivering Medical Devices," filed Oct. 13, 2009.

Paul et al.; U.S. Appl. No. 12/578,447 entitled "Medical Devices and Delivery Systems for Delivering Medical Devices," filed Oct. 13, 2009.

Salahieh et al.; U.S. Appl. No. 12/777,161 entitled "Two-Part Package for Medical Implant," filed May 10, 2010.

\* cited by examiner

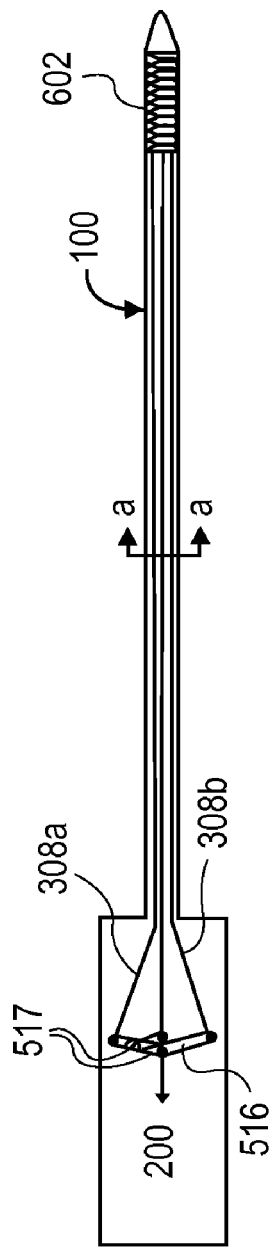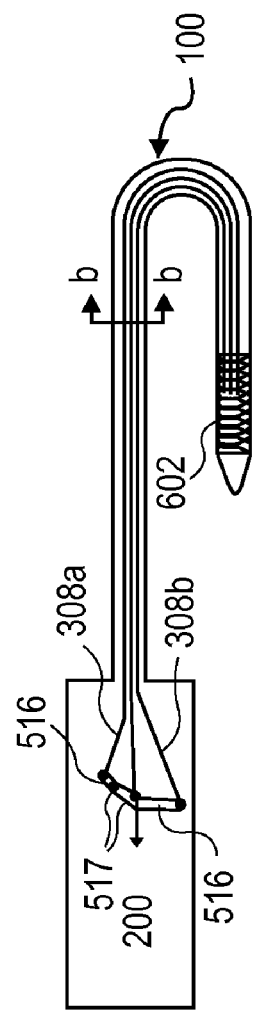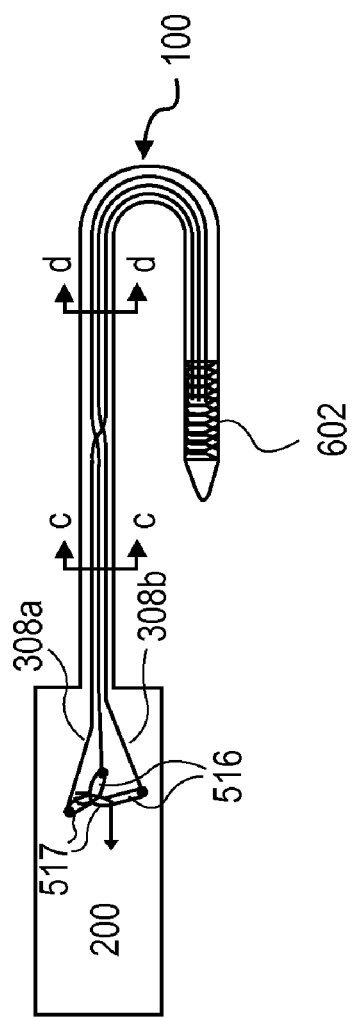

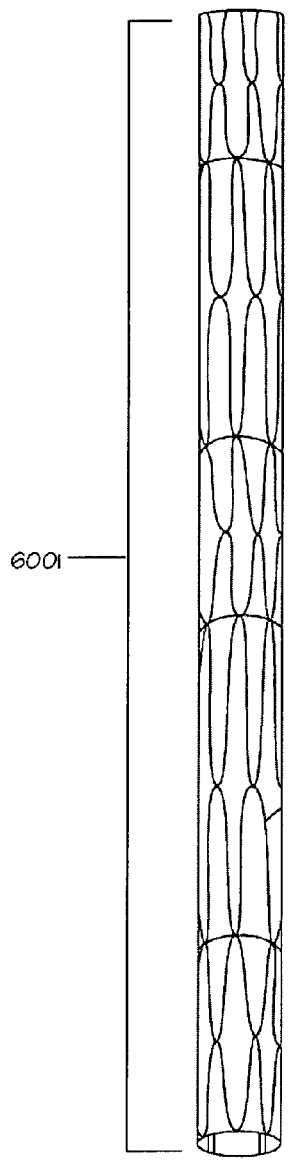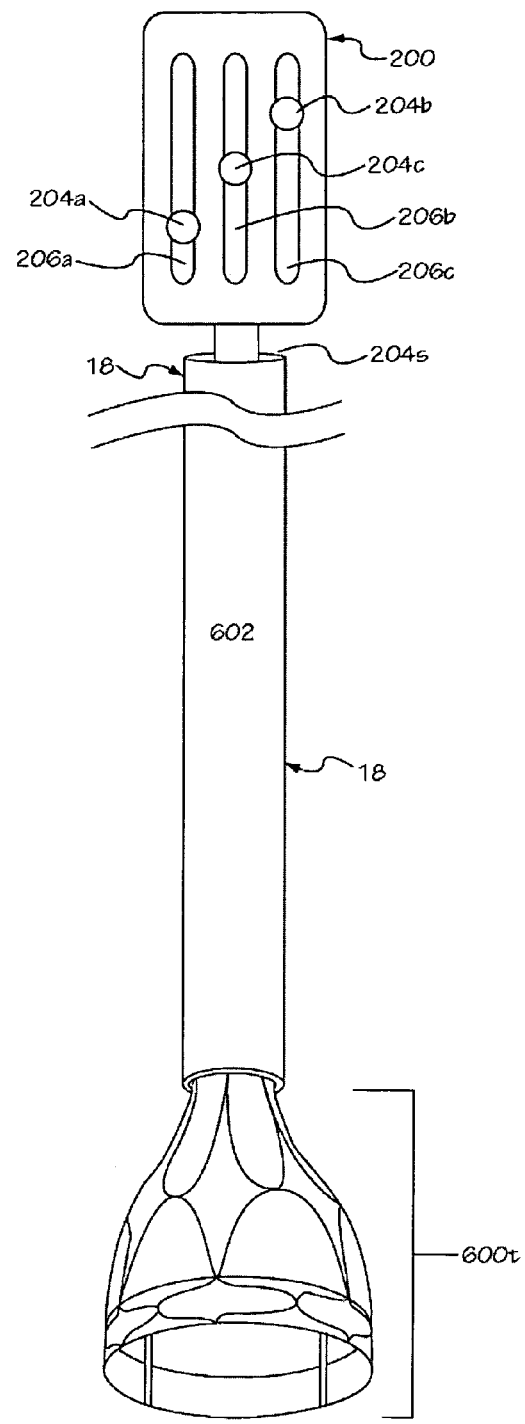
FIG 10A
FIG 10B

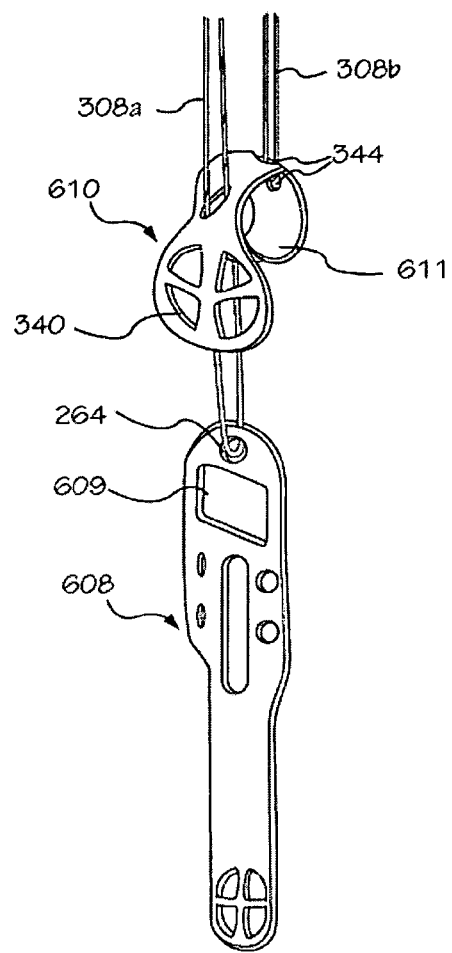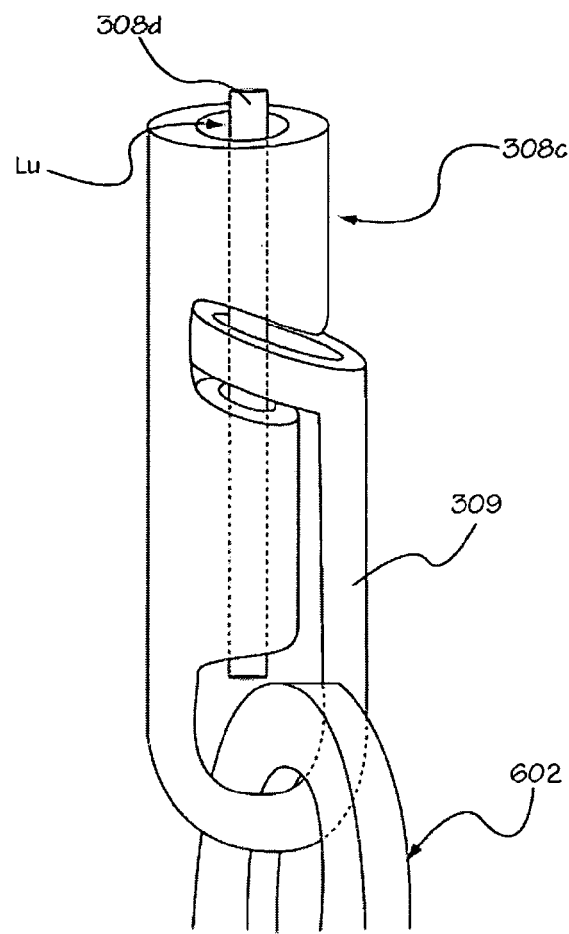
FIG 11A
FIG 11B

MEDICAL IMPLANT DEPLOYMENT TOOL

BACKGROUND OF THE INVENTION

The present invention relates principally to a system for the delivery and deployment of a replacement heart valve. Heart valve surgery is used to repair or replace diseased heart valves. Valve surgery is an open-heart procedure conducted under general anesthesia. An incision is made through the patient's sternum (sternotomy), and the patient's heart is stopped while blood flow is rerouted through a heart-lung bypass machine.

Valve replacement may be indicated when there is a narrowing of the native heart valve, commonly referred to as stenosis, or when the native valve leaks or regurgitates. When replacing the valve, the native valve is excised and replaced with either a biologic or a mechanical valve. Mechanical valves require lifelong anticoagulant medication on to prevent blood clot formation, and clicking of the valve often may be heard through the chest. Biologic tissue valves typically do not require such medication. Tissue valves may be obtained from cadavers or may be porcine, equine, bovine, or other suitable material, and are commonly attached to synthetic rings that are secured to the patient's heart.

Valve replacement surgery is a highly invasive operation with significant concomitant risk. Risks include bleeding, infection, stroke, heart attack, arrhythmia, renal failure, adverse reactions to the anesthesia medications, as well as sudden death. Two to five percent of patients die during surgery.

Post-surgery, patients temporarily may be confused due to emboli and other factors associated with the heart-lung machine. The first 2-3 days following surgery are spent in an intensive care unit where heart functions can be closely monitored. The average hospital stay is between 1 to 2 weeks, with several more weeks to months required for complete recovery.

In recent years, advancements in minimally invasive surgery and interventional cardiology have encouraged some investigators to pursue percutaneous replacement of the aortic heart valve. Percutaneous Valve Technologies ("PVT") Inc., has developed a balloon-expandable stent integrated with a bioprosthetic valve. The stent/valve device is deployed across the native diseased valve to permanently hold the valve open, thereby alleviating a need to excise the native valve and to position the bioprosthetic valve in place of the native valve. PVT's device is designed for delivery in a cardiac catheterization laboratory under local anesthesia using fluorscopic guidance, thereby avoiding general anesthesia and open-heart surgery. The device was first implanted in a patient in April of 2002.

PVT's device suffers from several drawbacks. Deployment of PVT's stent is not reversible, and the stent is not retrievable. This is a critical drawback because improper positioning too far up towards the aorta risks blocking the coronary ostia of the patient. Furthermore, a misplaced stent/valve in the other direction (away from the aorta, closer to the ventricle) will impinge on the mitral apparatus and eventually wear through the leaflet as the leaflet continously rubs against the edge of the stent/valve.

Another drawback of the PVT device is its relatively large cross-sectional delivery profile. The PVT system's stent/valve combination is mounted onto a delivery balloon, making retrograde delivery through the aorta challenging. An antegrade transseptal approach may therefore be needed, requiring puncture of the septum and routing through the mitral valve, which significantly increases complexity and risk of the procedure. Very few cardiologists are currently trained in performing a transseptal puncture, which is a challenging procedure by itself.

Other prior art replacement heart valves use self-expanding stents as anchors. In the endovascular aortic valve replacement procedure, accurate placement of aortic valves relative to coronary ostia and the mitral valve is critical. Standard self-expanding systems have very poor accuracy in deployment, however. Often the proximal end of the stent is not released from the delivery system until accurate placement is verified by fluoroscopy, and the stent typically jumps once released. It is therefore often impossible to know where the ends of the stent will be with respect to the native valve, the coronary ostia and the mitral valve.

Also, visualization of the way the new valve is functioning prior to final deployment is very desirable. Visualization prior to final and irreversible deployment cannot be done with standard self-expanding systems, however, and the replacement valve is often not fully functional before final deployment.

Another drawback of prior art self-expanding replacement heart valve systems is their lack of radial strength. In order for self-expanding systems to be easily delivered through a delivery sheath, the metal needs to flex and bend inside the delivery catheter without being plastically deformed. In arterial stents, this is not a challenge, and there are many commercial arterial stent systems that apply adequate radial force against the vessel wall and yet can collapse to a small enough diameter to fit inside a delivery catheter without plastically deforming.

However when the stent has a valve fastened inside it, as is the case in aortic valve replacement, the anchoring of the stent to vessel walls is significantly challenged during diastole. The force to hold back arterial pressure and prevent blood from going back inside the ventricle during diastole will be directly transferred to the stent/vessel wall interface. Therefore the amount of radial force required to keep the self expanding stent/valve in contact with the vessel wall and not sliding will be much higher than in stents that do not have valves inside of them. Moreover, a self-expanding stent without sufficient radial force will end up dilating and contracting with each heartbeat, thereby distorting the valve, affecting its function and possibly migrating and dislodging completely. Simply increasing strut thickness of the self-expanding stent is not a practical solution as it runs the risk of larger profile and/or plastic deformation of the self-expanding stent.

U.S. patent application Ser. No. 2002/0151970 to Garrison et al. describes a two-piece device for replacement of the aortic valve that is adapted for delivery through a patient's aorta. A stent is percutaneously placed cross the native valve, then a replacement valve is positioned within the lumen of the stent. By separating the stent and the valve during delivery, a profile of the device's delivery system may be sufficiently reduced to allow aortic delivery without requiring a transseptal approach. Both the stent and a frame of the replacement valve may be balloon-expandable or self-expanding.

While providing for an aortic approach, devices described in the Garrison patent application suffer from several drawbacks. First, the stent portion of the device is delivered across the native valve as a single piece in a single step, which precludes dynamic repositioning of the stent during delivery. Stent foreshortening or migration during expansion may lead to improper alignment.

Additionally, Garrison's stent simply crushes the native valve leaflets against the heart wall and does not engage the leaflets in a manner that would provide positive registration of the device relative to the native position of the valve. This increases an immediate risk of blocking the coronary ostia, as well as a longer-term risk of migration of the device post-implantation. Further still, the stent comprises openings or gaps in which the replacement valve is seated post-delivery. Tissue may protrude through these gaps, thereby increasing a risk of improper seating of the valve within the stent.

One potential solution to these issues is the development and use of a repositionable heart valve, as has been described in U.S. patent application Ser. No. 10/746,280 filed on Dec. 23, 2003 entitled "Repositionable Heart Valve and Method." The contents of that application are herein incorporated by reference. The repositionable heart valve resolves numerous issues presented by Garrison's stent. However deploying and redeploying the heart valve is not without its own set of technical challenges.

One challenge with using mechanical elements to connect the user control with an implantable device and/or its delivery system is assuring that the user controls properly actuate the mechanical components of the system, particularly when the deployment tool or catheter navigates the tortuous path from its insertion point to the deployment location, such as the heart. For example, some deployment systems use multiple actuators elements extending along at least part of the path from insertion point to deployment location to perform the deployment function. Bends, twists, and rotations in the catheter can cause internal physical path lengths to vary widely.

If differences in actuator path lengths are not properly compensated for, the operation of the deployment tool may not be predictable. For instance, some actuators may have a shorter path length to the implant and its deployment mechanism than others. If all the actuators are used simultaneously, the operator would expect an even distribution of the deployment operation. Instead those paths that are shorter might function sooner, while those that are longer might operate later. The reverse is also true if the shorter lengths are overly relaxed due to slack in the actuation elements, while the longer path ways are taut because the actuation elements are strained because of the longer path length. In either scenario, the operation and deployment become unpredictable and unreliable. If stresses on the actuation elements are too great, they may cause deformation or distortion of the implant before any of the actuation elements are even used. This could result in serious complications that may require invasive procedures to intervene.

SUMMARY OF THE INVENTION

Thus it is an objective of the present invention to provide for a system capable of deploying a replacement heart valve where the system has a compensation mechanism for correcting path length differences among the mechanical actuation elements.

It is another objective of the present invention to provide a system able to exert the needed actuation forces for both deployment, and redeployment of the replacement heart valve.

Yet another objective is to provide for a deployment system having a reliable actuator system for safely delivering the proper level of forces to the implant and the deployment mechanism that the implant requires.

There is still another need for a method of operating such a system to provide safe and effective steps to handle the deployment of a replacement heart valve or other vascular implant.

One or more of the objectives above are met using an implant system comprising an implant, and a deployment tool adapted to deploy the implant. The deployment tool comprises an actuation controller and a plurality of elements adapted to apply forces to one or more implant deployment mechanism(s). Each actuation element is adapted to extend along an actuation element path within a patient's vasculature. There is also an actuation element compensation mechanism adapted to compensate for differences in length between the actuation element paths.

There is also a method for deploying an implant using the system of the present invention. The method comprises the steps of first endovascularly delivering an implant and implant deployment mechanism to an implant site. Second applying an actuation force to the implant deployment mechanism through actuation elements extending through the patient's vasculature while compensating for differences in length between actuation element path lengths to deploy the implant.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 8A-J illustrate additional compensation mechanisms.

FIGS. 10A-E illustrates an implant deployment.

FIGS. 11A-B provide an illustration of implant and actuation element details according to alternative embodiments of the invention.

DETAILED DESCRIPTION OF THE INVENTION

Figure 1A:
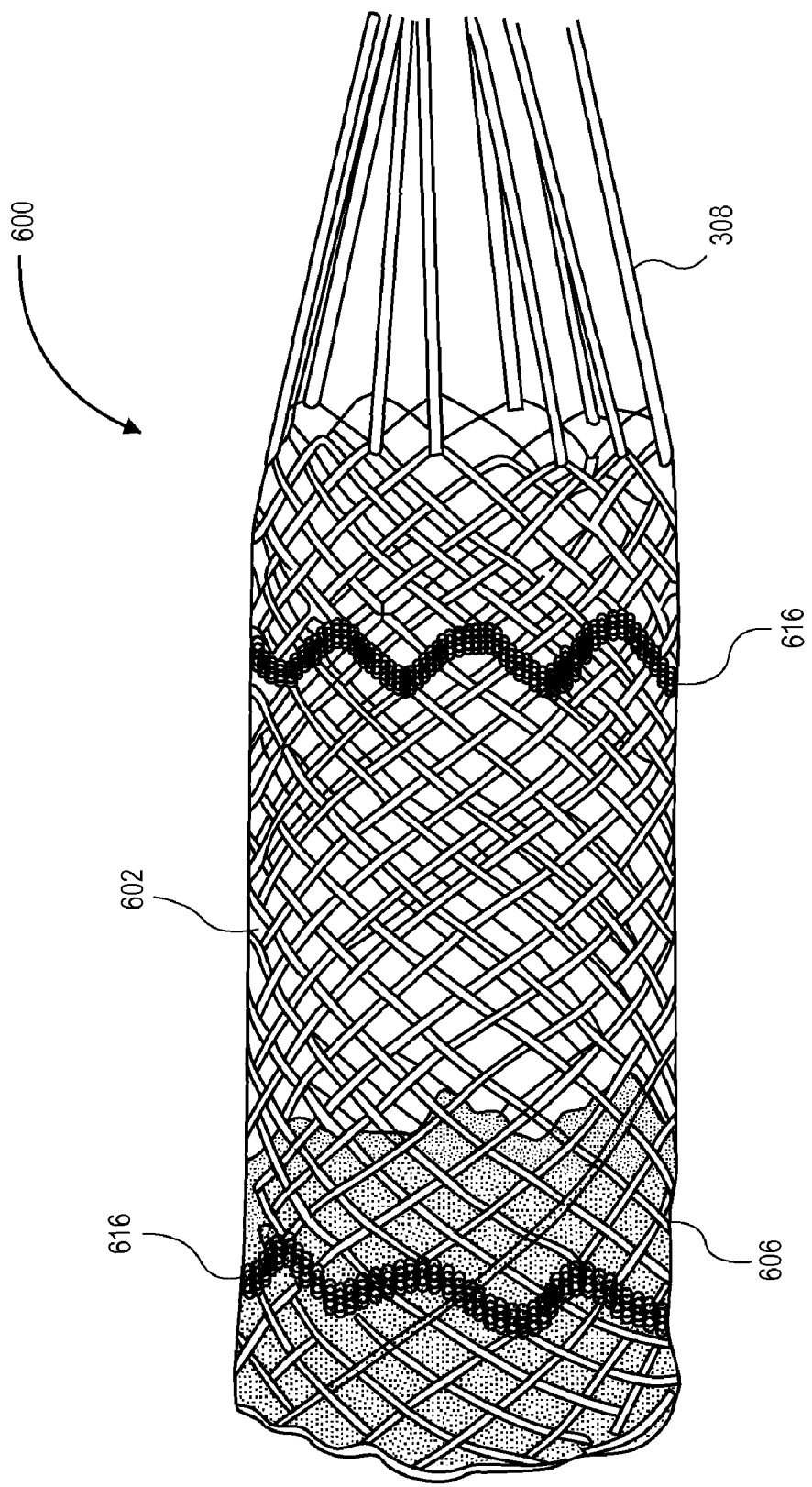
FIG. 1A shows an implant to be used with the present invention.

The invention is drawn to methods, mechanisms and tools for the endovascular deployment of medical implants, such as replacement heart valves. According to some embodiments of the invention, the deployment process includes actuating one or more actuation elements to control and/or perform actions of the implant deployment mechanism, or mechanical elements of the implant itself. The operation of the implant deployment mechanism or the mechanical elements of the implant are often fully reversible, allowing a physician to partially deploy and then reverse the deployment operation of ("undeploy") the implant. This provides the ability to reposition and redeploy the implant. As a general reference, the orientation of the system is referred to as is traditional for a medical device catheter. The proximal end is nearest the physician or operator when the system is being used. The distal end is furthest away from the operator and is in the patient's vasculature. To facilitate imaging of the implant during a procedure, the deployment tool may have a lumen for providing a contrast agent to the site where the implant is being positioned within the patient's body.

One embodiment of the invention provides an implant system having an implant adapted for endovascular delivery and deployment and a deployment tool adapted to deploy the implant. The implant of the present invention can be any suitable for deployment into the human body. Possible implants envisioned for deployment with the present system are those previously described in co-pending U.S. patent application Ser. No. 10/746,280 entitled "REPOSITIONABLE HEART VALVE," filed on Dec. 23, 2003; Ser. No. 10/893,131 entitled "METHODS AND APPARATUS FOR ENDOVASCULARLY REPLACING A PATIENT'S HEART VALVE" field on Jul. 15, 2004; Ser. No. 10/893,151 entitled "METHODS AND APPARATUS FOR ENDOVASCULARLY REPLACING A PATIENT'S HEART VALVE" filed on Jul. 15, 2004; Ser. No. 10/746,120 entitled "EXTERNALLY EXPANDABLE HEART VALVE ANCHOR AND METHOD" filed on Dec. 23, 2003; Ser. No. 10/746,285 entitled "RETRIEVABLE HEART VALVE ANCHOR AND METHOD" filed Dec. 23, 2003; Ser. No. 10/982,692 entitled "RETRIEVABLE HEART VALVE ANCHOR AND METHOD" filed on Nov. 5, 2004; Ser. No. 10/746,872 entitled "LOCKING HEART VALVE ANCHOR" filed on Dec. 23, 2003; and Ser. No. 10/870,340 entitled "EVERTING HEART VALVE" filed on Jun. 16, 2004. Additional forms of a replacement heart valve implant will be illustrated herein.

The deployment tool is designed to deliver the implant to an implant site and to deploy the implant, such as described in the above referenced patent application(s). In some embodiments, the deployment is controlled through actuation elements which are connected to actuators (such as knobs, levers, etc.) in an actuation controller (such as a handle). When a user exerts force on an actuator, by either pushing or pulling the actuator, the actuation element conveys a force to whatever the actuation element is connected to, such as an implant deployment mechanism or the implant. For minimally invasive implant procedures (percutaneous, endovascular, laparoscopic, etc.), the actuator controller and actuators are often remote from the actuated implant. In addition, the path from actuator to implant—the path along which the actuation elements extend—may be other than a straight line. For example, the delivery tool for a percutaneous endovascular delivery of a replacement heart valve may extend through the arterial vasculature from an opening in the patient's femoral artery at the thigh to the patient's aorta, a route that has multiple bends and turns. Because some of the deployment tool's actuation elements extend through a bent or turned section of the deployment tool, the path lengths through which various actuation elements need to operate may differ. It may therefore be desirable to compensate for these differences in path length, or to otherwise equate displacements and force of the actuation element paths.

In some embodiments, deployment is achieved when an operator uses the actuation controller to apply proximally or distally directed forces on the implant deployment mechanism. These forces are translated into displacements. Force is conveyed from the actuation controller through the actuation elements to an implant deployment mechanism. The actuation elements extend along actuation element paths. This invention provides an actuation compensation mechanism incorporated into the deployment tool that compensates for variations in length between actuation element paths.

The actuation controller is located on the proximal end of the deployment tool. The actuation controller may be a handle or gripping device having one or more actuators incorporated into it. The actuators may be, e.g., mechanical, fluid or electrical actuators.

The actuation elements may be, e.g., a material or substance used to convey force from the actuation controller to the implant deployment mechanism. Wires, threads (such as polymer threads) or sutures are examples of actuation elements used to provide direct mechanical linkage between the actuation controller and the implant. In other embodiments, the actuation elements may have a fluid component. Other possible applications for the actuation element include the use of electromechanical or electromotive components. Another alternative is the use of shape memory alloys that can be electrically or thermally actuated.

The actuation element paths may be along individual lumens (one for each actuation element), or there may be a lesser number of lumens than actuation element paths (e.g., where multiple actuation elements share a lumen). All actuation elements may share a single path, in which case there is a single actuation element path extending from the actuation controller to the either the implant or the implant deployment mechanism. The actuation element paths may be sealed against the environment so that blood and other bodily fluids do not escape from the patient and to minimize contamination by outside environmental factors. The introduction of the deployment tool and the actuation paths may be similar to those techniques used to introduce catheters, laparoscopes, endoscopes, etc., into the body.

In some embodiments, the implant deployment system comprises a catheter, and the actuation elements are disposed within the catheter. It will be appreciated that there is no need for path length compensation where there is no differences in path length between two points. Thus the actuation element compensation mechanism does not have to adapt the path lengths for the entire length of the deployment tool or catheter. In some embodiments, path length compensation is therefore provided only in the sections of the deployment tool that actually experience actuation element path length differences.

For instance, if the deployment tool were to experience a substantial bend (such as when navigating the aortic arch), the path length differences between actuation elements on the outer curve of the deployment tool will be greater than those on the inside of the curve of the deployment tool in that section of the deployment tool and will be compensated for by this invention. In one embodiment, the actuation element paths extend in a spiral fashion about the long axis of the deployment tool. By rotating the actuation element paths about this axis so that each path completes at least a 360 degree rotation about the central axis over the bend area of the deployment tool, the effect of the bend is minimized since all actuation elements will experience the same path length over this region. It is not important for each actuation element path to have a uniform pitch across any length of the deployment tool or bend, only for each lumen to make an equal number of turns about the central axis over a given distance. If there are multiple regions along the length of the deployment tool where compensation will be needed, the deployment tool can be designed to provide the compensation necessary. For instance, there may be multiple sections of the deployment tool that have spiral actuation paths, as well as intermediate sections where the actuation element paths are substantially straight.

The correspondence of the actuation elements to the actuation element paths is such that the system may be designed so that the actuation element compensation mechanism comprises a catheter with a number of distinct actuation element lumens. In one embodiment, the actuation elements are disposed in a 1:1 ratio with the actuation element paths.

In yet another embodiment, the actuation controller incorporates the actuation element compensation mechanism. The actuation element compensation mechanism may be built into the actuation controller, the actuators or be a part adapted to be fitted onto the actuation controller during use.

One example of an actuation compensation mechanism incorporated into the actuation controller is the use of a fluid compensation device. Here the actuation element compensation mechanism is a manifold fluid reservoir combined with a number of pistons. Each piston is operatively connected to an actuation element, and each has a surface exposed to fluid from the reservoir. There may also be a source for pressurized fluid communicating with the reservoir. A movable wall or diaphragm can be adapted to be a movable wall to change the volume of the reservoir.

In still another embodiment, the actuation element compensation mechanism may comprise a movable mechanical linkage connected to the actuation elements. The mechanical linkage may be a single pivoting element, or a group of pivoting elements, a spring at the proximal end of each actuation element, or one or more pulleys. To facilitate the operation and movement of each actuation element, the system may incorporate an actuation element operation mechanism to permit each actuation element to be moved separately, in groups or in unison.

The actuation element compensation mechanism may be incorporated into the body of a catheter comprising at least two actuation element lumens. A first actuation element is disposed in a first lumen and a second actuation element is disposed in a second lumen.

In yet another alternative embodiment, the implant system is provided with a catheter type body with a prefabricated shape bent to approximate the expected bends in the anatomy through which it will be delivered. The actuation elements are set to different lengths at manufacture to accommodate the known different path lengths associated with the bend. The catheter would be sufficiently flexible to be deployed in a straightened configuration similar to other catheters for minimally invasive procedures; however the catheter would assume the prefabricated bent shape either through a controlled operation or through a natural tendency to assume the bent shape. Once the catheter is in the bent shape, the pre-set actuation element lengths offset the differing lengths of the actuation element paths through the catheter body. Thus if the first actuation element path is shorter than the second (or N value of actuation element paths) then the first actuation element is correspondingly shorter than the second actuation element (and so forth to the N value of actuation elements and paths).

In some embodiments, the deployment device may need very few actuation elements, or the actuation elements can be grouped while they traverse the actuation element paths. In this manner a plurality of actuation elements may be placed into a single lumen. The actuation element path will run substantially parallel to and offset from a central axis of the catheter.

The use of the system described above also entails a novel method for placing an implant where an actuation compensation mechanism must be used. The method of deploying an implant using the present system comprises the steps of first endovascularly delivering an implant and implant deployment mechanisms to an implant site, and second applying an actuation force to the implant deployment mechanisms through actuation elements extending through the patient's vasculature while compensating for differences in length between actuation element path lengths to deploy the implant.

The compensating step may involve moving a proximal end of one actuation element proximal to a proximal end of another actuation element. The moving step may involve applying fluid pressure to a piston surface operatively connected to each actuation element. The compensating step may also involve locking relative positions of the proximal ends of the actuation elements prior to the applying step.

Alternatively, the compensating step may involve moving a proximal end of one actuation element distal to a proximal end of another actuation element. Here the moving step may involve applying fluid pressure to a piston surface operatively connected to each actuation element. Once again, this may entail locking relative positions of the proximal ends of the actuation elements prior to the applying step.

In another alternative embodiment, the applying step may involve moving a hinged mechanical linkage to with proximal ends of the actuation elements are operatively connected. Instead of a hinged mechanical linkage, the step may be moving a mechanical linkage operatively connected to proximal ends of the actuation elements through a pulley.

In still another embodiment, the applying step may involve moving a mechanical linkage operatively connected to proximal ends of the actuation elements through springs.

The system and methods may be used to deploy any suitable implant into a patient; however the systems as described below are discussed primarily in association with the preferred embodiment, in which the implant is a replacement heart valve.

In referring to the accompanying drawings, a variety of conventions are used in the labeling of the many parts. Among the many parts of the present system some are labeled using alphabet scripts in addition to numerical labels. The convention of "number+letter" denotes there are multiple numbers of this part. For instance, actuation elements are labeled as 308a-n. A reference to the collective whole of actuation elements is referred to simply as 308. Where there are multiple discrete actuation elements shown in the drawings, these appear as 308a, 308b, 308c, etc. . . . The letter variables a-n denote a first part beginning with the letter "a" and going to an indefinite number of parts "n". The letter "n" here does not denote the 14th letter of the alphabet and thus limit the part sequence to a maximum of 14 duplications of the part. "n" is used in the sense of a mathematical variable for as many multiples of a part as are needed. Furthermore, the drawings as presented are not to scale, either to each other or internally, but instead are offered in a manner to provide clearer illustration of the various embodiments and elements discussed herein.

The system of the present invention is designed to deliver and deploy an implantable device. Specifically the system is adapted to deliver and deploy an implantable device using a plurality of mechanical actuation elements in mechanical communication with the implant itself, as well as any number of additional deployment elements. By way of example, and for illustration purposes only, the present invention may be adapted and used with a radially expandable and foreshortening anchoring mechanism to help secure the placement of a replacement heart valve. An example of such a replacement is herein provided in FIG. 1A. Viewed here is an implantable device 600 being connected to the deployment tool through a set of radially disposed interface elements or fingers. Additionally actuation elements extend from the body of the deployment tool and connect to various actuatable portions of the implant 600. The implant may also have a prosthesis, such as a valve, disposed within it.

The detailed assembly of the implant may follow a number of design parameters and uses. One embodiment of an implant that may be used with the system of the present invention is described in U.S. patent application Ser. No. 10/746,280, entitled REPOSITIONABLE HEART VALVE AND METHOD and filed on Dec. 23, 2003. The implant has been reproduced herein in FIGS. 1A-C. The implant 600 has two major components, an anchor 602 and a replacement heart valve 606. Optionally, radiopaque bands 616 may be added to the implant to enhance viewing of the implant under fluoroscopy. The implant 600 can be deployed using a distal mechanical deployment device 402 located substantially on the end of the deployment tool. The anchor has a relatively long and narrow length 600i (FIG. 10A) in its pre-deployment state compared to its fully deployed state 600f (FIG. 10E).

Figures 1B, 1C:
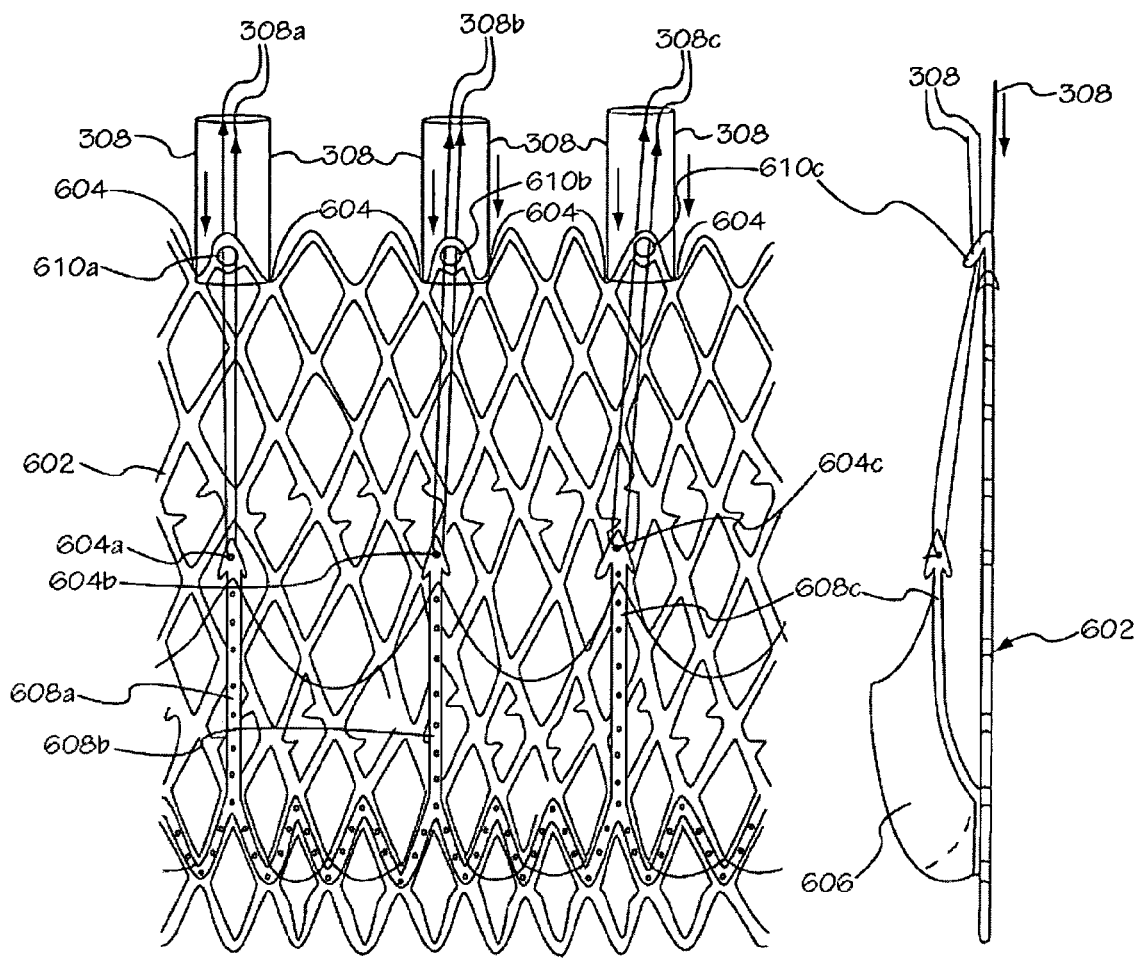
FIG. 1B-C illustrate two cut away views of the implant.

The actuation elements described herein are illustrated with various interface points in the implant. FIG. 1B shows the implant cut open and laid flat; actuation elements 308 can be seen connecting to the lattice network of the anchor 602. Additional actuation elements 308a, 308b, 308c are shown interfacing with paired posts 608a, 608b, 608c and buckles 610a, 610b, 610c. The actuation elements 308, 308a-c can be surgical threads, wires, rods, tubes or other mechanical elements allowing for the mechanical linking of the actuators in the handle or actuation controller and the various components of implant 600 and/or its delivery system, such as posts 608, buckles 610. In operation, some of the actuation elements shown 308a, 308b, 308c may be drawn up so the posts attached to the actuation elements are drawn into and through the buckles 610a, 610b and 610c. The actuation elements 308 interface with the implant or deployment mechanism at various actuation element interface sites 604. While the posts are being drawn through the buckles, the anchor 602 goes through a foreshortening process to expand the radius of the anchor. When the anchor 602 is foreshortened to a deployed configuration, the posts are drawn up to lock in place with the buckles.

The deployment of the anchor is a fully reversible process until the lock has been locked via, e.g., mating a male interlocking element with a female interlocking element. After locking, deployment is completed by decoupling the actuation elements from the anchor.

Figure 2:
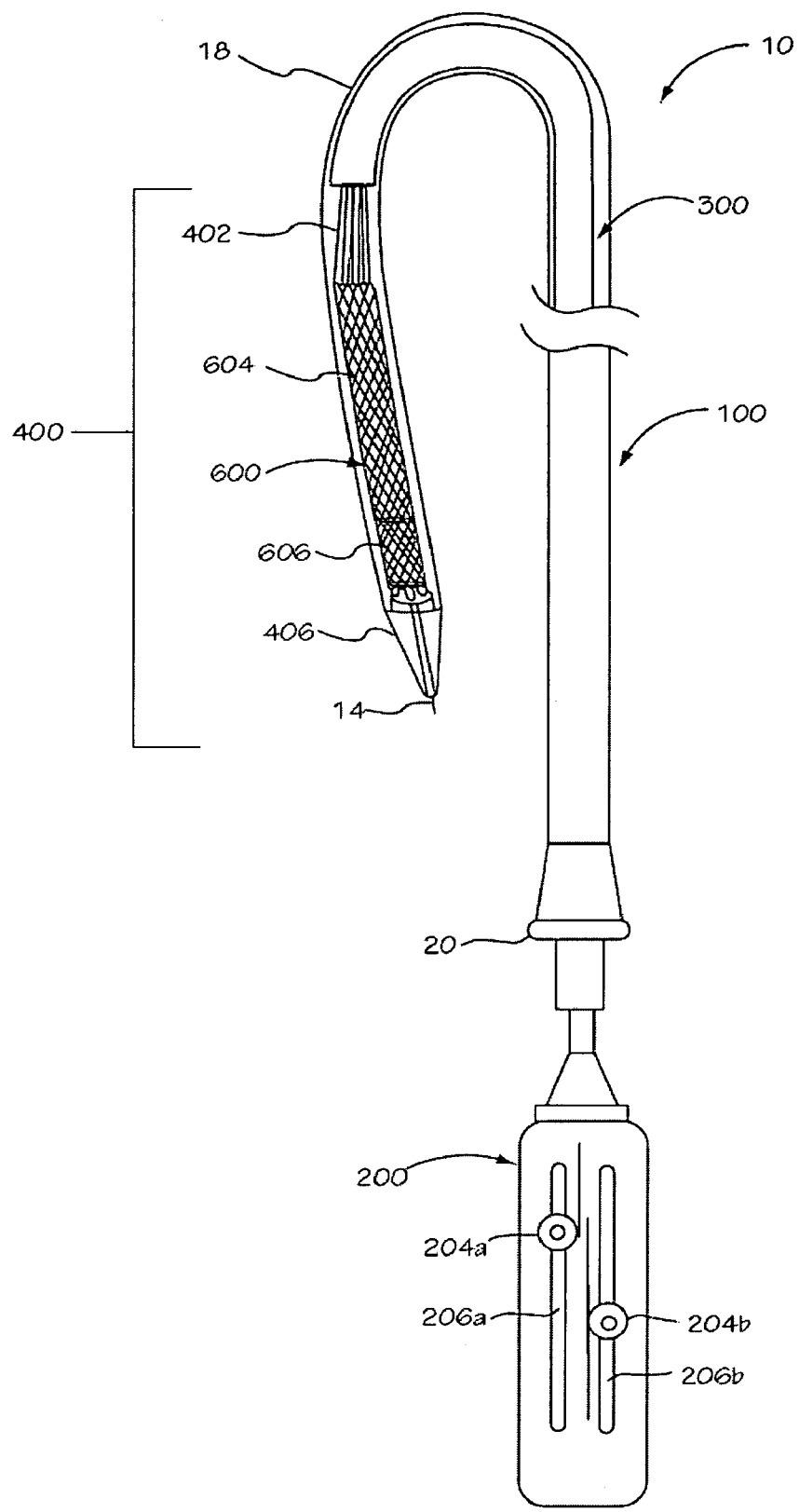
FIG. 2 provides an illustration of the system.
Figure 3A:
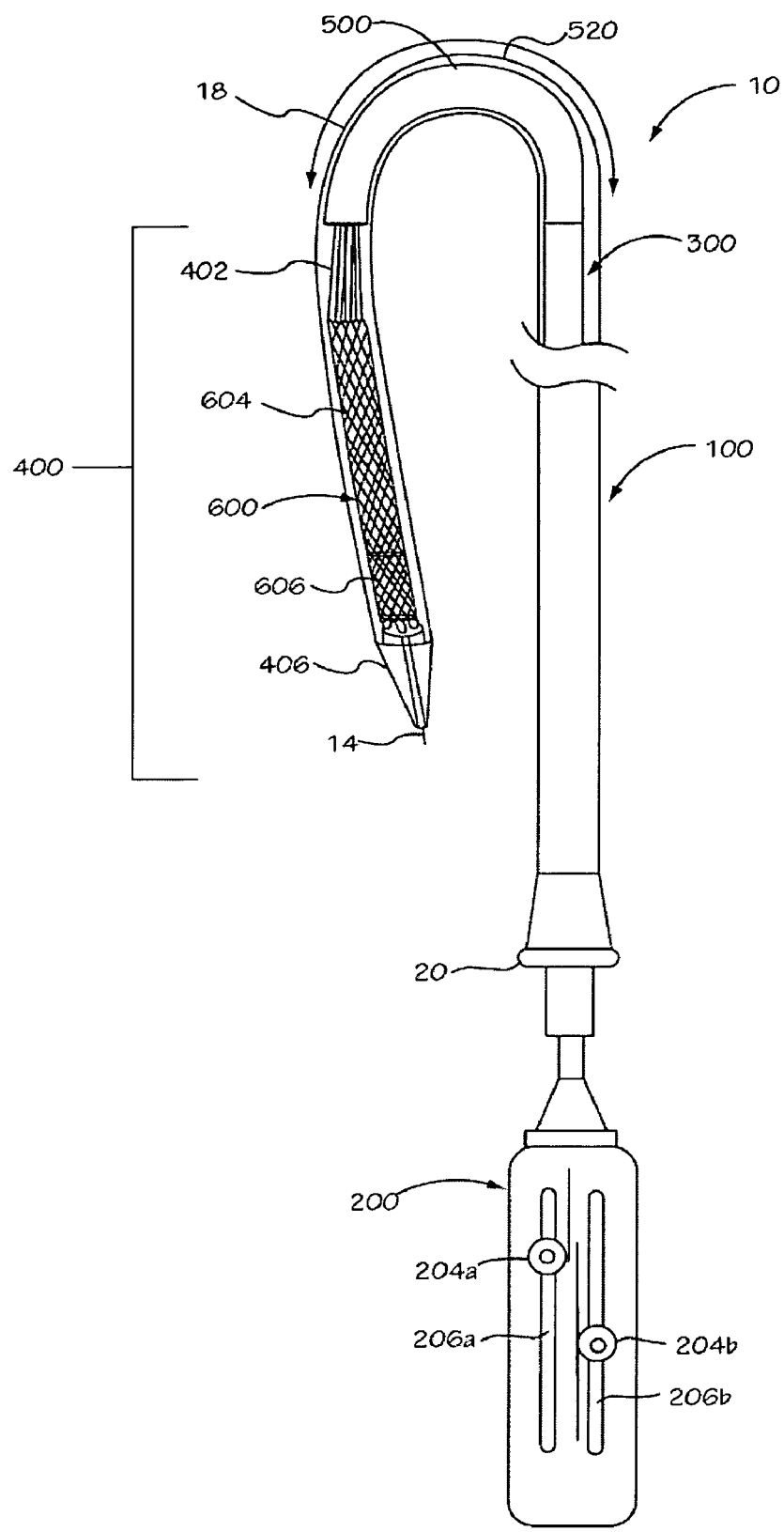
FIG. 3A shows one embodiment of an actuation element path length compensation

FIGS. 2 and 3A show an implant system 10 designed to deploy an implant 600, such as a replacement heart valve 606 and anchor 604. Actuators 204a, 204b are movable in corresponding sliders 206a, 206b in the actuation controller 200 of a deployment tool 100 and provide an appropriate amount of force and/or displacement to the implant 600, to an implant deployment mechanism (that is, e.g., part of the deployment tool itself), and/or to release mechanisms at the actuator element/implant interfaces or at the actuator element/deployment mechanism interfaces regardless of path length differences taken by the actuation elements of the deployment tool 100 during a medical procedure. The deployment tool 100 has a deployment tool body 300 and an outer sheath 18. In one example, when deploying a replacement heart valve from the femoral artery through the aorta and across the aortic arch, a length of the deployment tool must bend nearly 180 degrees to make the placement possible as shown in FIG. 3A. This bend region 520 of the deployment tool 100 is where the actuation element path lengths begin to vary, with the effect realized at the distal end 400. The actuation element compensation mechanism 500 compensates for path length differences that result from this bend. As shown, the system 10 also has a guide wire lumen 114 (FIG. 3B) for slidably receiving a guide wire 14, a nose cone 406 for facilitating advancement of the system 10 through the vasculature, an outer sheath 18, and an outer sheath advancement actuator 20.

The actuation element compensation mechanism may be a mechanical arrangement of the actuation element paths over the length of a bend region, or it may be a mechanism designed to compensate through a flexible and adaptable adjustment system regardless of changes in path length during usage. The compensation mechanism may be positioned in the bend, proximally or distally. Though some embodiments are more advantageous than others depending on circumstances and environment, all are contemplated as alternative embodiments of the present invention.

Figure 4:
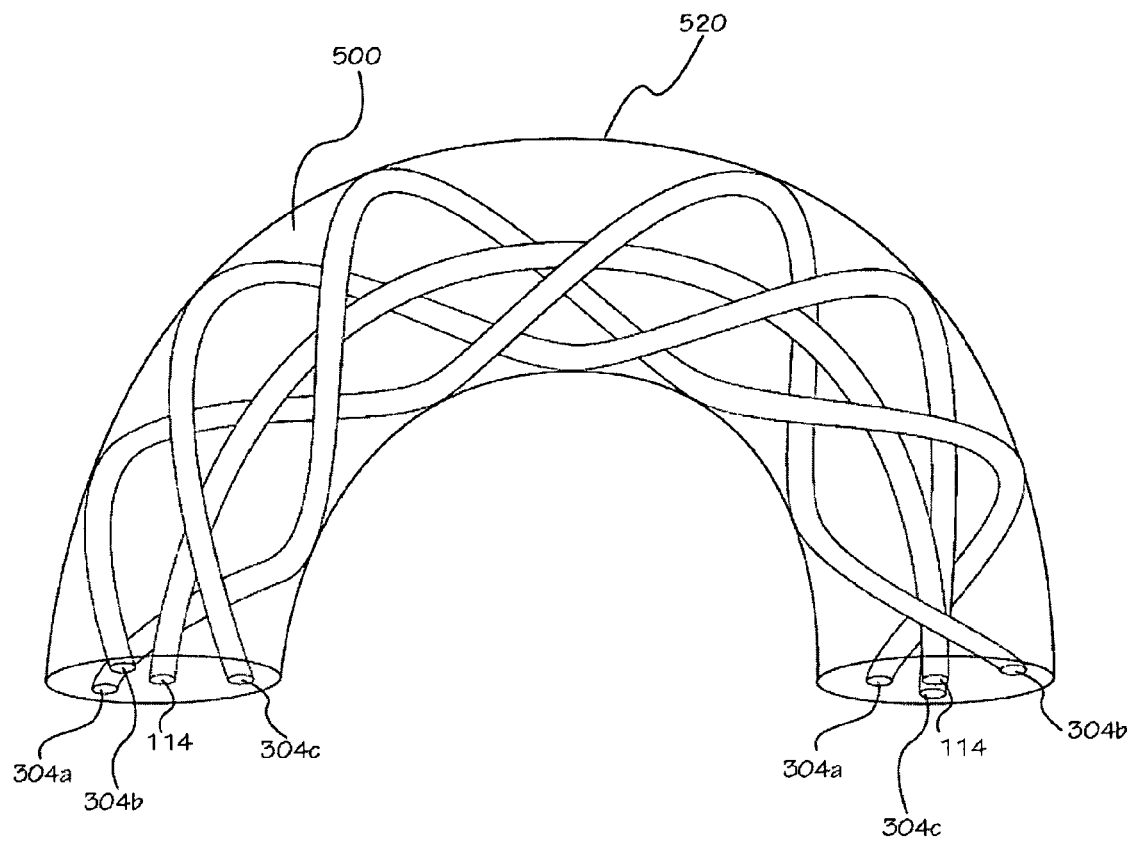
FIG. 4 illustrates a multiple actuation element compensation mechanism.

FIG. 4 is an expanded view of the region 520 from FIG. 3A. Here the actuation element compensation mechanism 500 takes the form of winding the actuation element paths 306a, 306b, 306n in a spiral fashion about the central guide wire lumen 114. The number of actuation element paths that may be wound about the center is limited only by the physical size of the deployment tool 100.

Figure 3B:
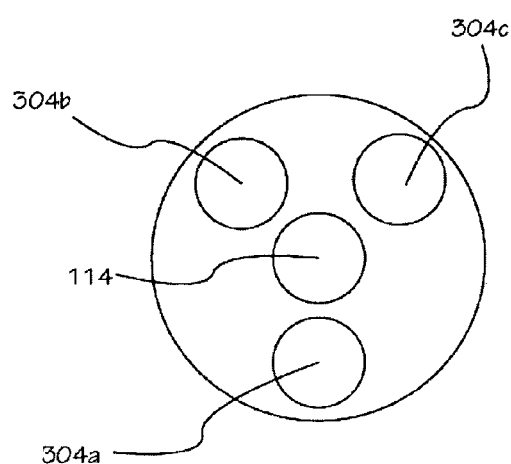
FIG. 3B illustrates a cross section of the deployment tool.

The construction of the deployment tool uses technologies and materials as are appropriate for medical device catheters. The positioning of the various actuation element paths within the deployment tool may be fixed or variable. In one embodiment, the position of the various actuation element paths 308a, 308b, 308n are fixed and shown in cross section (FIG. 3B). This is accomplished by an extrusion process for making the core of the deployment tool body. A polymer material, such as PEBAX™, may be used to make the core. The core is extruded having the desired number of lumens. Beside the lumens that serve as the actuation element pathways 308, there may be additional lumens as are needed for placement and use of the deployment tool.

Figure 3C:
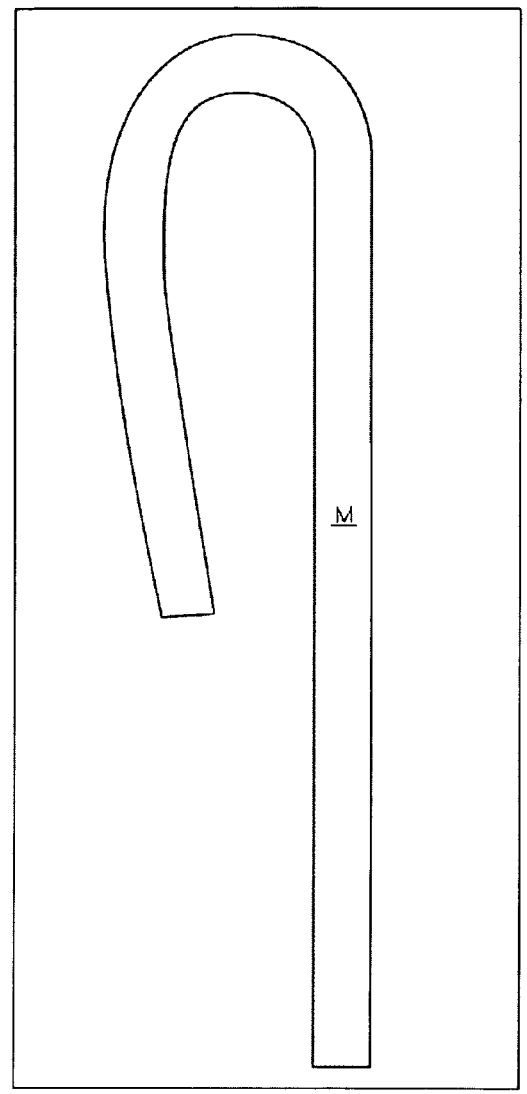
FIG. 3C illustrates a mold used in manufacturing the actuation element path length compensation section.

Once the core has been extruded, a fixed length is cut and prepared for shape setting. The shape setting involves threading each lumen with a PTFE coated, stainless steel mandrel. Then the core along with the mandrels are twisted so the lumens rotate about the central axis a desired number of rotations. The preferred rotations for the actuation element paths is 360-540 degrees (one to one-and-a-half twists). The twisted core is fed into a shaped metal mold M and baked in an oven to heat set the desired bend and twists into the core (FIG. 3C). Once this process is complete, the core is removed from the oven and allowed to cool. The twisted core is mated to a straight core section and welded together so the lumens match from the twisted heat set section, to the normal extruded section. The normal extruded section has a higher durometer value than the twisted section, to provide enhanced pushability during use.

Once the twisted section and the straight section are mated together properly, the core containing the actuation element pathways is combined with a braided wire heat set outer sheath. The sheath can be used to provide added guidance and movement control of the deployment tool during deployment, as well as radial compression force on the implant deployment mechanism and/or the implant. Overall the diameter of the deployment tool that is inserted into the body is 24 French or less. Preferably the diameter is 21 French or less.

Although the above description calls for an extruded core, it is also practical to make the core using a variety of other catheter building techniques. For instance, individual lumens may be designed and arranged in cable-like manner so the twisting of the actuation element paths occurs by winding individual lumens together. Alternatively the actuation element paths may be formed from a series of gap spaces in an axial layering arrangement. Additional methods may be readily apparent to those skilled in the art of catheter manufacturing.

Figure 5:
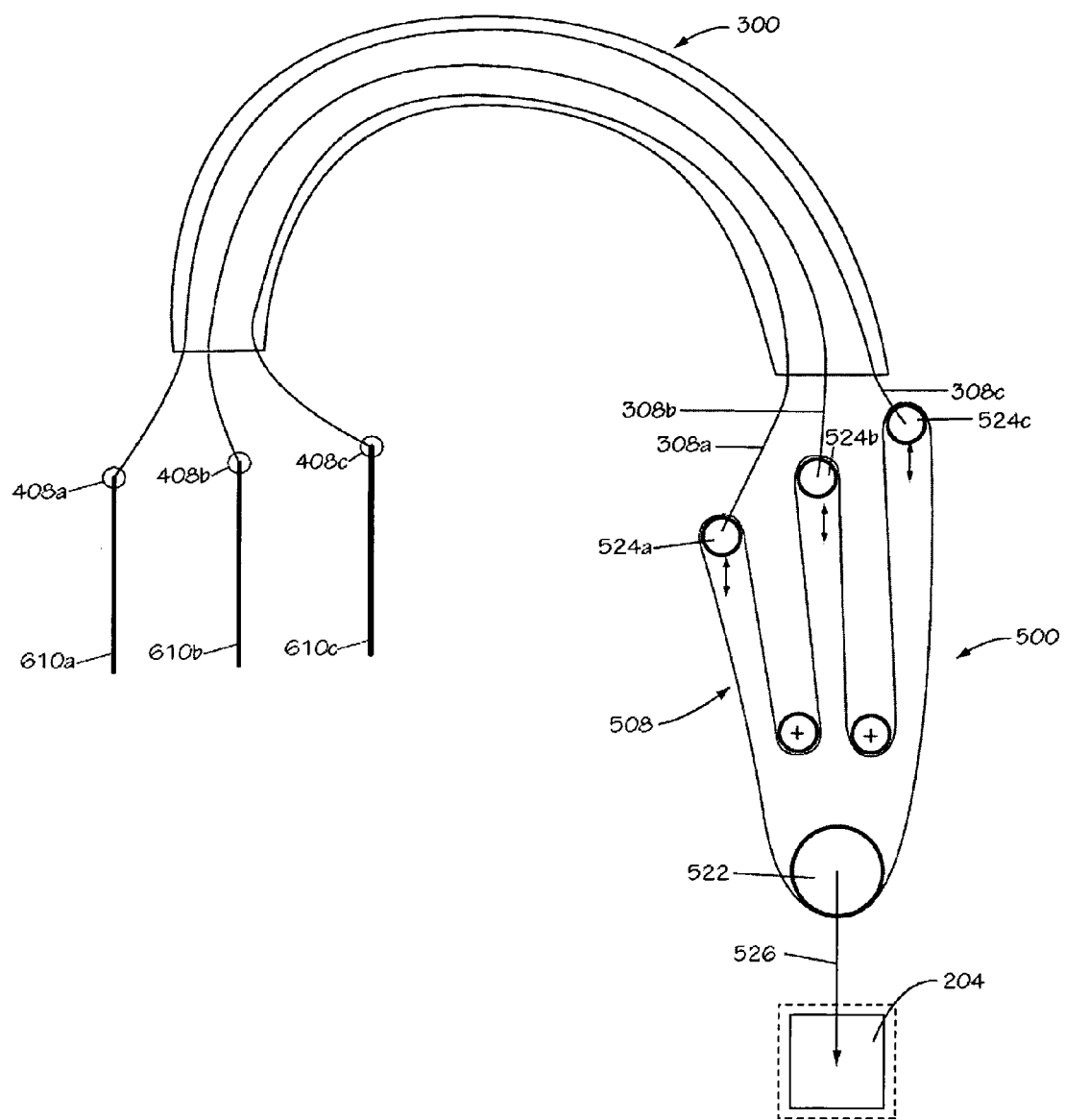
FIG. 5 shows a pulley style compensation mechanism.

In another embodiment, the actuation element compensation mechanism 500 uses a pulley and tackles 508 arrangement (FIG. 5). The pulley 522 can be controlled through an actuator 204. As the pulley line 526 is stretched tight through the actuator, the tackles 524a-c move in corresponding fashion to take up the slack in the pulley compensation device 508 and the actuation elements 308 extending through the deployment tool body 300. Once the slack in the actuation elements is taken up, the actuator 204 can exert force on the connectors 408a, 408b, 408c to pull the buckles 610a, 610b, 610c of the implant proximally.

Figure 6A:
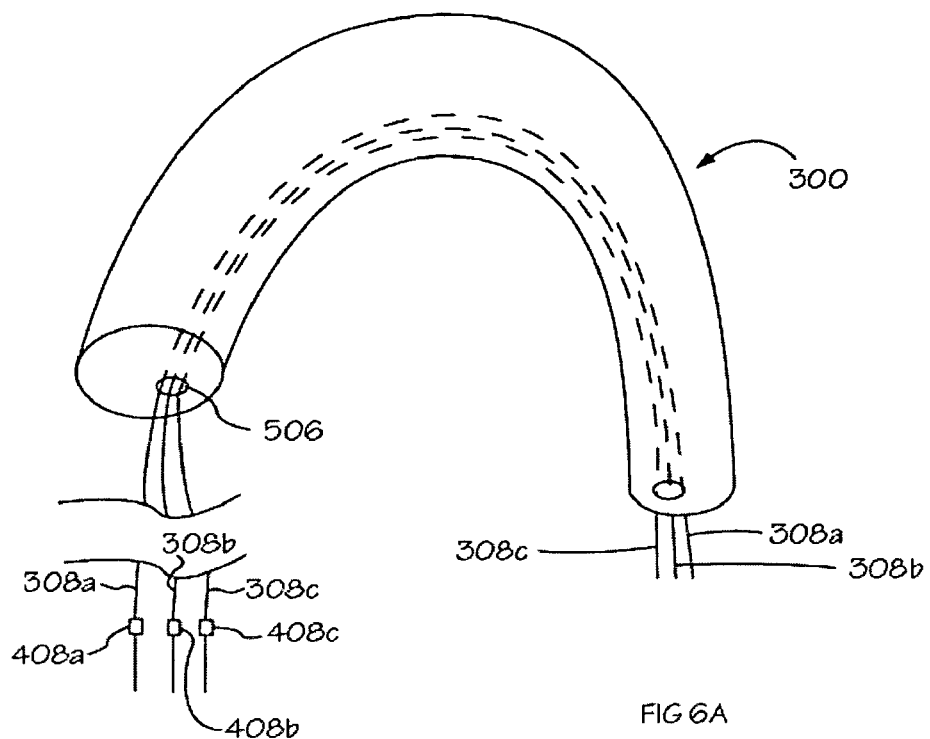
FIGS. 6A-B show an actuation element path length compensation mechanism using a common path for multiple actuation elements.
Figure 6B:
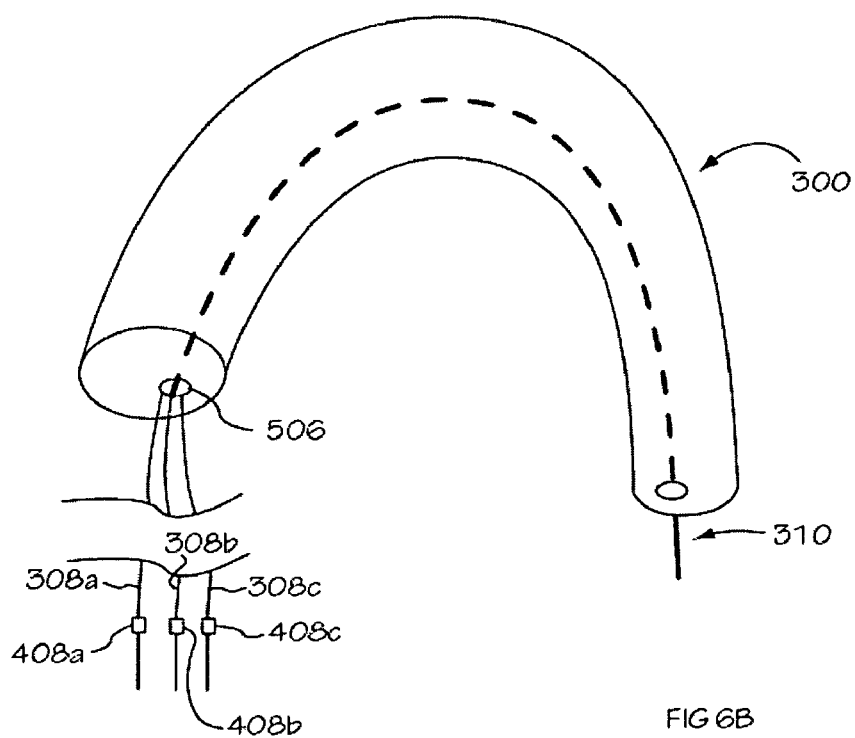

In another embodiment there are numerous actuation element interface sites 408a-c to the deployment mechanism or the implant (FIG. 6A-B). There is at least one actuation element 308a-c linked to each actuation element interface site 408a-c. To at least partially compensate for differences in path length from the interface sites to the actuator, the actuation elements are disposed along a single actuation element path, such as by placing all actuation elements within a single lumen 506. The actuation elements may also be bundled together, either into a single line 310 such as a cable, or bundled to move together as a single unit in a harness so that the actuation elements reduce to a single primary actuation element extending to the proximal end to be linked to a single actuator 204. It is possible when using low friction materials, such as a Teflon® coated polymer thread, or other suitable material, that the individual actuation elements may be harnessed into a single unit 310. Instead of being intertwined, the individual elements are laid side by side with a minimal amount of twining or braiding. Then at the actuation controller, each actuation element 308a-n is separated out and linked to an individual actuator 204a-n. In this manner it is possible to construct the same relationship of actuators 204 and actuation elements 308 and actuation element interface sites 408 without having to construct numerous actuation element paths.

Figure 7:
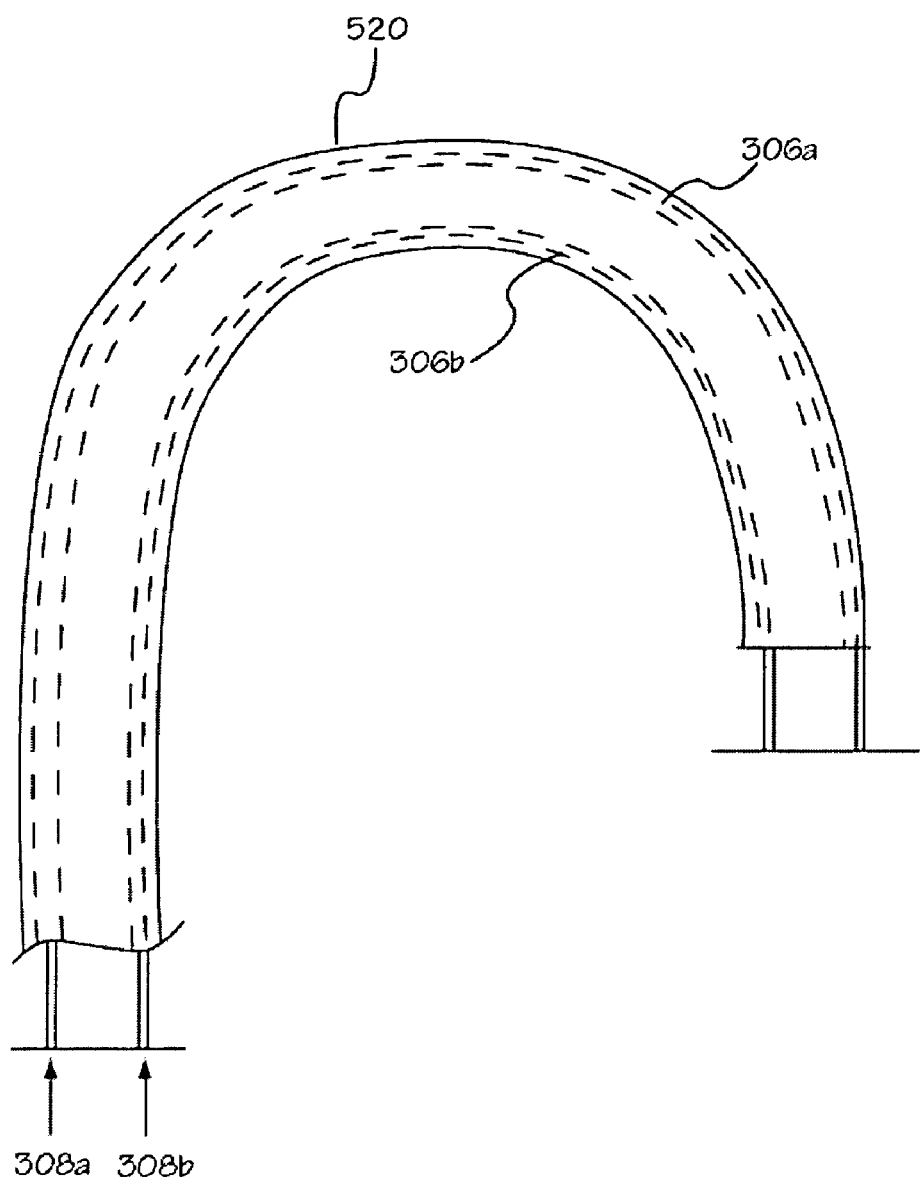
FIG. 7 shows a length style compensation mechanism.

In still another embodiment, if the deployment tool is configured for a particular application in the body where the bend is of a known length and angle, the individual actuation elements 308 can be preformed to correspond to the path lengths associated with the bend (FIG. 7). Here there are two actuation elements 308a, 308b traversing two actuation element paths 306a, 306b respectively. So long as the bend 520 of the deployment tool remains substantially the same during deployment in the human body as the manufactured shape, this embodiment will operate reliably. If there are variations that may be involved, a secondary actuation element compensation as described herein may be combined with the preformed path length embodiment. In this embodiment, the path length compensation mechanism takes the form of preformed actuation element lengths when the system is manufactured.

Many variations are possible. If the system is in a neutral position, the path lengths extending from the actuation controller to the implant are the same length. No compensation is needed until the deployment tool and its accompanying actuation elements are bent to conform to a body lumen. In one alternative embodiment shown in FIG. 8B, the illustrative actuation elements 308a-c are shown with three different arc lengths. When the curvature of the deployment tool in the human body is known or can be estimated with sufficient accuracy, the actuation elements 308a-c can be prefabricated so the actuation element paths are of the appropriate length between the distal end 400 and the actuation controller 200 as well as any associated mechanical device 600 located distally. The actuators 204a, 204b, 204c can be pre-positioned in a manner to allow for proper engagement of the actuation elements once the deployment tool is properly positioned, or the actuators may be movable so their positions adjust during deployment. In this manner the actuators 204 are able to automatically adjust to the changes in path length with the actuation elements during the deployment of the deployment tool. The actuation elements in this embodiment may be set into the actuation element pathways in order to prevent any kinking or bunching up of the actuation element length while the deployment tool is stored in a neutral state, or is flexed into a neutral state (such as when the tool is first deployed into the human body).

It is also possible for each actuation element to have a separate actuation element compensation mechanism directly linked to the actuation elements so that a different compensation mechanism can be used for different parts of the deployment system. For example, one actuation element compensation mechanism may work well for the release of the actuation elements that interface with the deployment mechanism while a different compensation mechanism will interface well with the actuation elements associated with actuation of the implant. Another actuation element compensation mechanism may be used with the actuation elements used to disengage the operable actuation elements from the implant in order to make the final deployment of the implant. In this embodiment, the various actuation elements have two or more compensation mechanism types. The actuation element compensation mechanisms are identified as generic box components 500a-c shown in FIG. 8C allow for the incorporation of any of the compensation mechanisms described herein to be adapted to the actuation element as provided in the drawing.

In another embodiment (FIG. 8D), a pulley system 508 can be used as the actuation element compensation mechanism 500. In this embodiment the operation of the actuator 204 causes the withdrawing of a first pulley 522a. The first pulley 522a has a first actuation element 308a engaged about its surface. As the actuator is moved, the pulley is drawn back and forth in the actuation controller 200. The proximal end of the actuation element 308a is engaged to a second pulley 522b. When the first pulley 522a is moved via the actuator 204, the first pulley will be drawn up until the tension in the line is equal throughout its length. When the first pulley has used up the slack in the first actuation element, the proximal end of the actuation element begins to operate on a second pulley. The second pulley 522b now moves in response the force requirements of the first actuation element to ensure all the actuation elements are taut before the deployment of the implant begins. A variety of combinations are possible allowing for one actuator to control one or more set of pulleys while having multiple actuators to control multiple actuation elements. The actuators may cooperate to control multiple actuation elements for one distal component of the system, or to control more than one distal component using one or more actuator for each distal component to be controlled.

In still another embodiment, the actuation element compensation mechanism may be a set of springs 508a-n. (FIG. 8E). The springs 518 are used as an interface between the actuators 204 and the actuation elements 308. As the system is deployed through a patient vasculature, the springs extend from a resting position to provide additional path length to the actuation elements that require additional length to handle the bend in the deployment tool. The springs 508 are connected on their distal ends to the actuation elements while the proximal ends are connected to one or more actuators 204. Once the deployment tool 100 is properly placed in a patient's vasculature, the actuators can be engaged to operate the various components on the distal end. If the springs have additional slack that needs to be taken up before the individual actuation elements are taut, then the actuators may be moved so as to exhaust the slack in each spring line, or the actuator may possess an additional feature to absorb slack. For instance, the actuator may rotate like a spool to take up slack in the actuation element and spring connection. Alternatively, the spring may have a spring tension low enough to allow it to yield during deployment, but high enough to operate as a continuation of the actuation element itself when the actuator is engaged. In a third embodiment the actuator may engage the spring element and the actuation element. In this manner the actuator can withdraw the spring, or exhaust the slack in the spring before engaging the actuation element. The spring may be attached to a movable piece that the operator may withdraw from the system while manually affixing the actuator to the actuation element for operation.

Figure 8A:
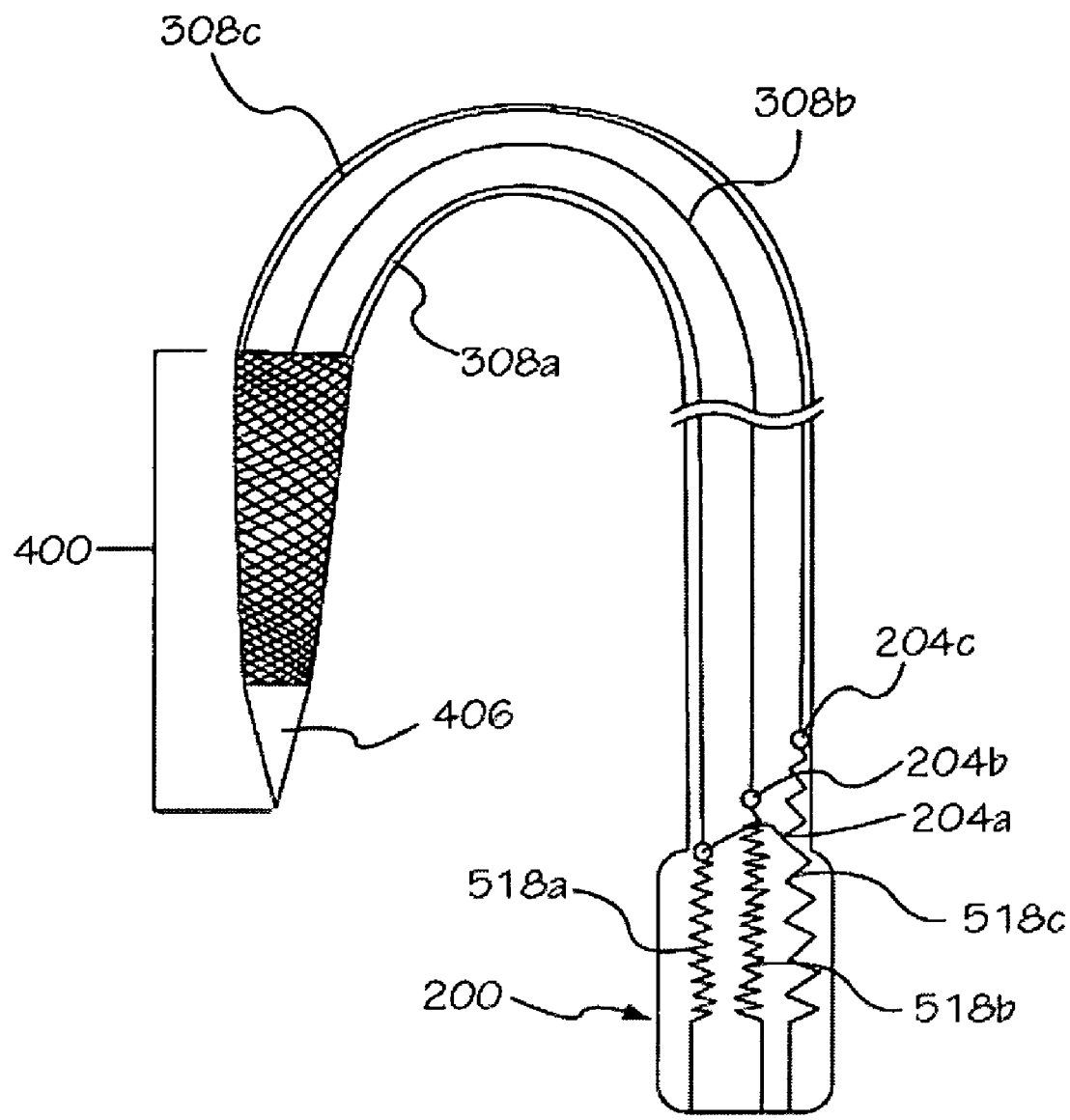
Figure 8B:
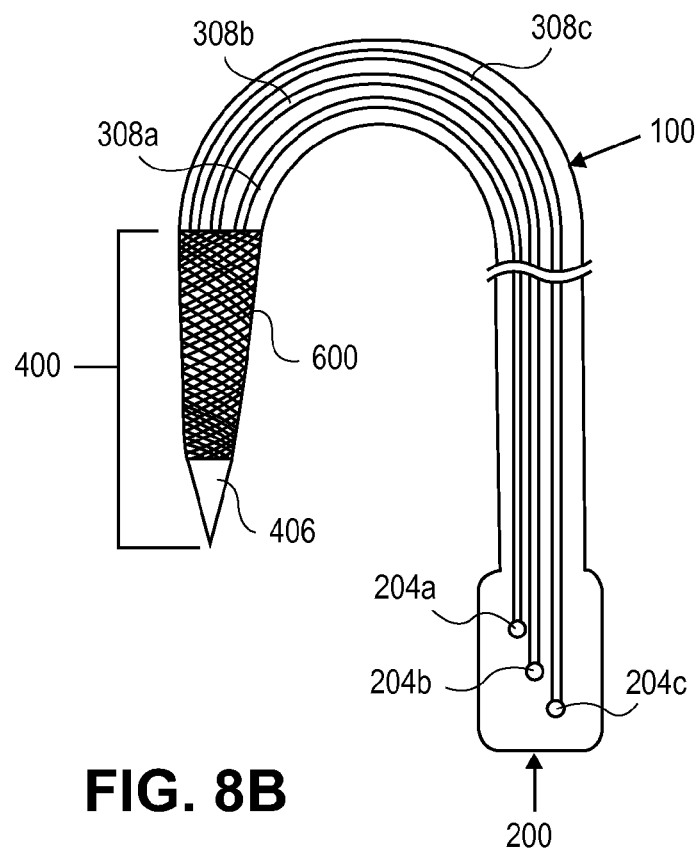
Figure 8C:
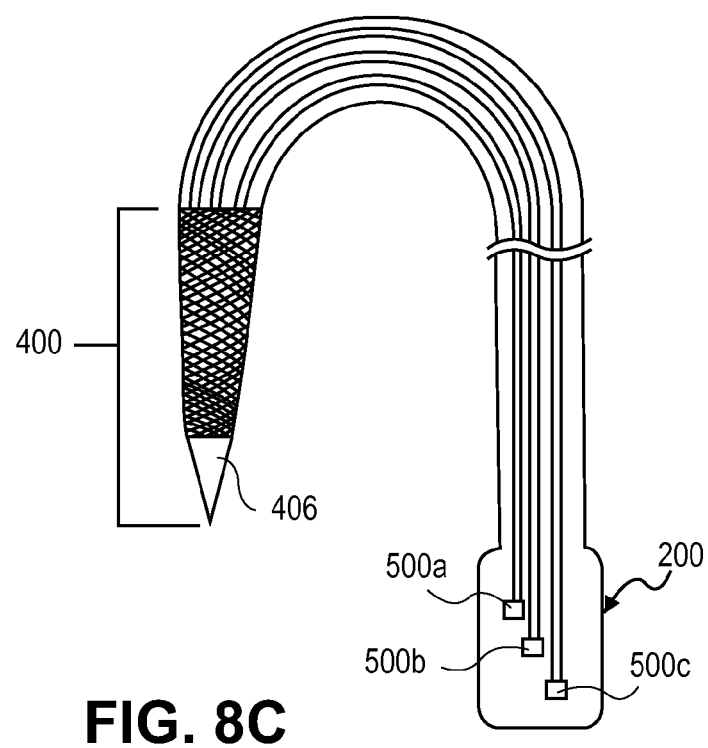
Figure 8D:
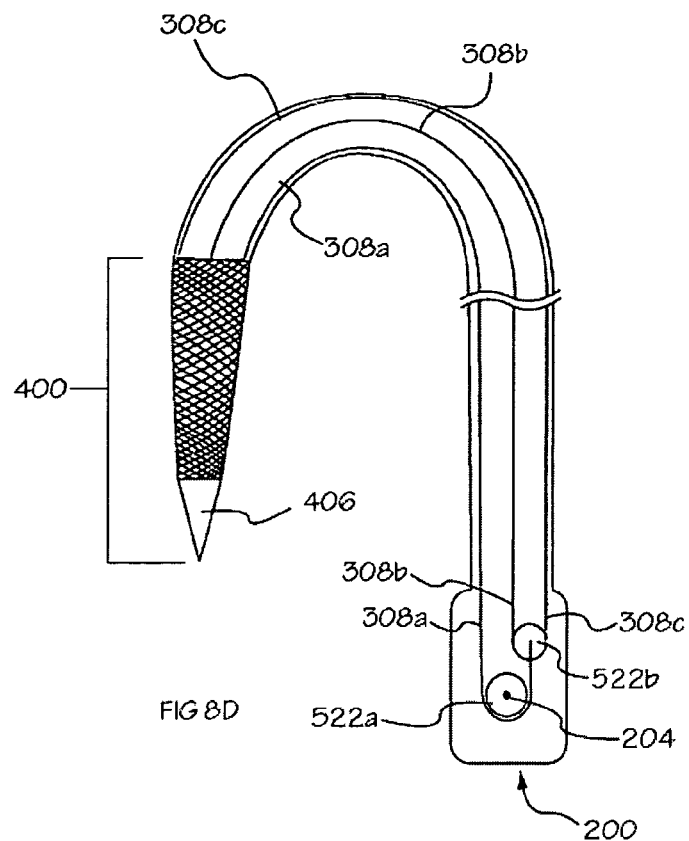
Figure 8E:
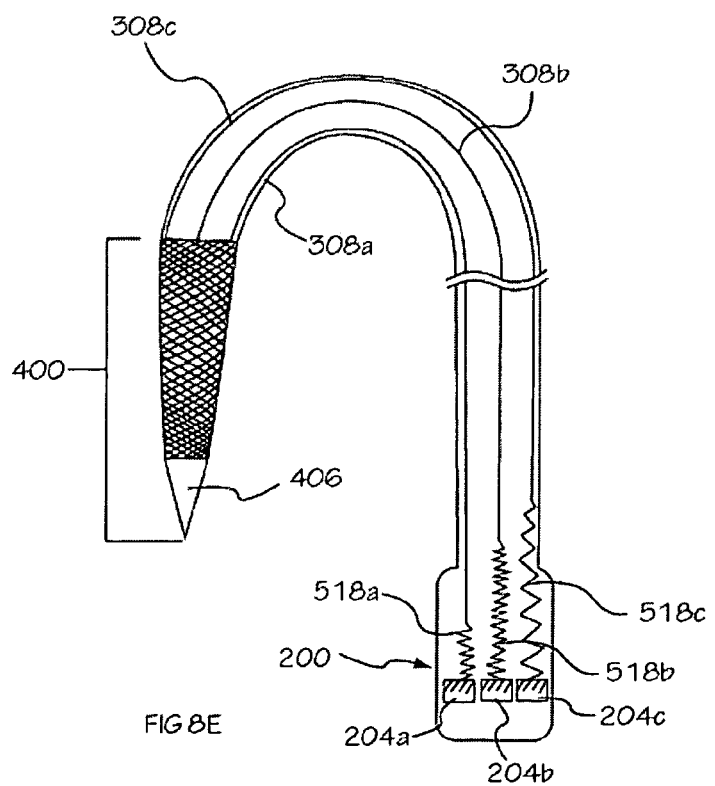

In another embodiment, the actuators 204 may be positioned between the actuation elements 308 and the springs 518 (FIG. 8A). In this embodiment, the actuators are not constrained during the placement of the deployment tool into a patient's vasculature. In this manner the springs 518 may compensate for path length differences by extending in axial length and providing additional length as needed. Once the implant is properly positioned, the actuators are already located on the distal end of the taut actuation elements 508. The actuators 204 may now be engaged without any further operations or manipulations to ensure the actuation elements are taut and the actuation element pathways have been properly compensated for.

In another embodiment, the actuation element compensation mechanism 500 may be a mechanical linkage (FIGS. 8F-H). In one embodiment there is a two bar linkage system used in the actuation controller 200. The two bar linkage 516 has at least one proximal interface for being controlled by an actuator. The two bar linkage may have spring resistance or tension incorporated into its pivot joints 517. The pivot joints 517 serve to provide path length compensation for the actuation elements 308a-n as the actuation controller 200 is being used. Each of the bars in the two bar configuration will pivot such that the ends which experience the least force will pivot in a proximal direction. The end experiencing the least force will be that connected to the actuation element providing the least resistance or having the most slack, as associated with a shorter path length. When the resistance of the actuation elements is substantially equal, any further movement of the actuator will cause all the actuation elements to pull equally on the distal end. Once again, actuation elements may be connected to one or more sets of linkages like a additional two bar linkage.

Once the deployment tool 100 is bent (FIG. 8G) the mechanical linkage 516 flexes as described above to provide path length compensation. The mechanical linkage 516 can be combined with other path length compensation mechanisms to provide further length compensation, as in the event where the linkage 516 is combined with a series of helically wound actuation element pathways. (FIG. 8H).

Figure 8I:
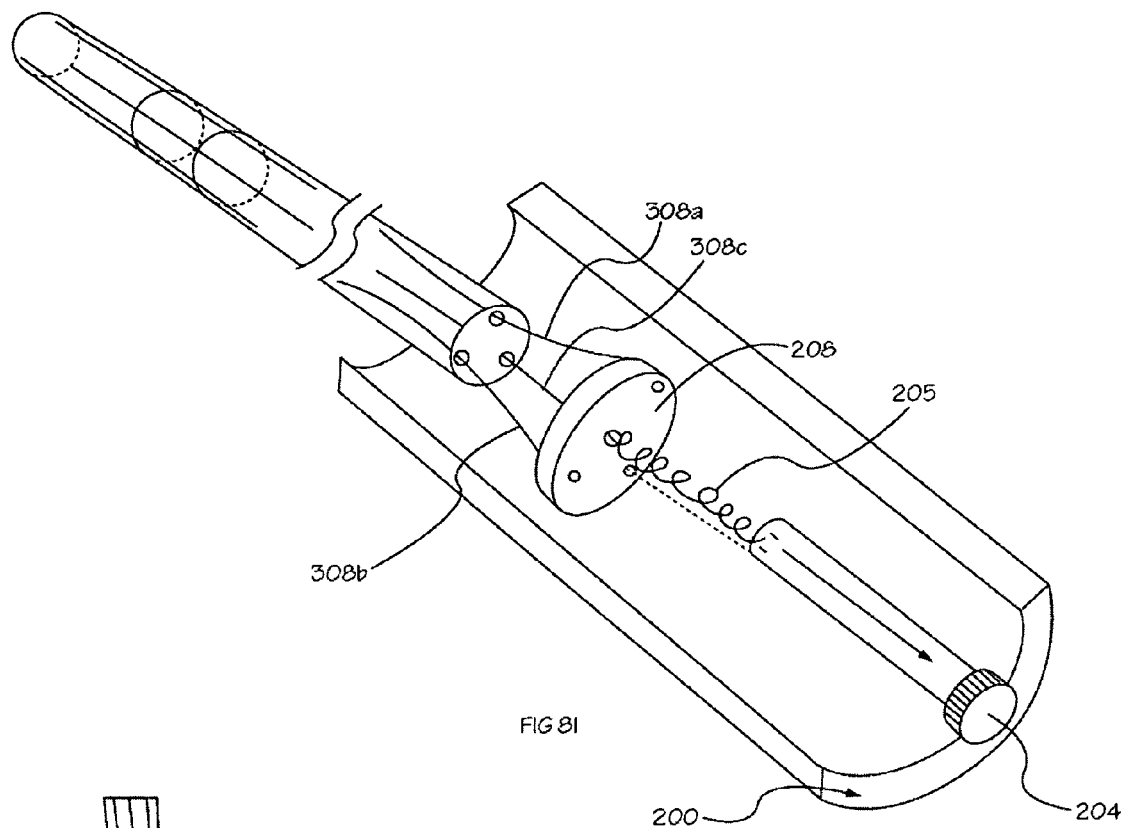

Alternatively, the path length compensation mechanism may be a centrally pivoted plate 208 (FIG. 8I). In this embodiment the plate 208 is connected to the actuation elements 308a-c distally and to an actuator interface 205 proximally. The actuator interface 205 provides preload in the operation of the actuator 204. In other embodiments (not shown) the actuation interface may be replaced with a u joint or ball joint or other multiple degrees of freedom capable joints. When the actuator is withdrawn or advanced in actuation controller 200, the plate 208 moves proximally or distally with the actuator. The plate will pivot such that the edge which experiences the least force will pivot in a proximal direction. The edge experiencing the least force will be that connected to the actuation element providing the least resistance or having the most slack, as associated with a shorter path length. The plate 208 may be constructed in a variety of different configurations, allowing for small or large differences in path length.

Figure 8J:
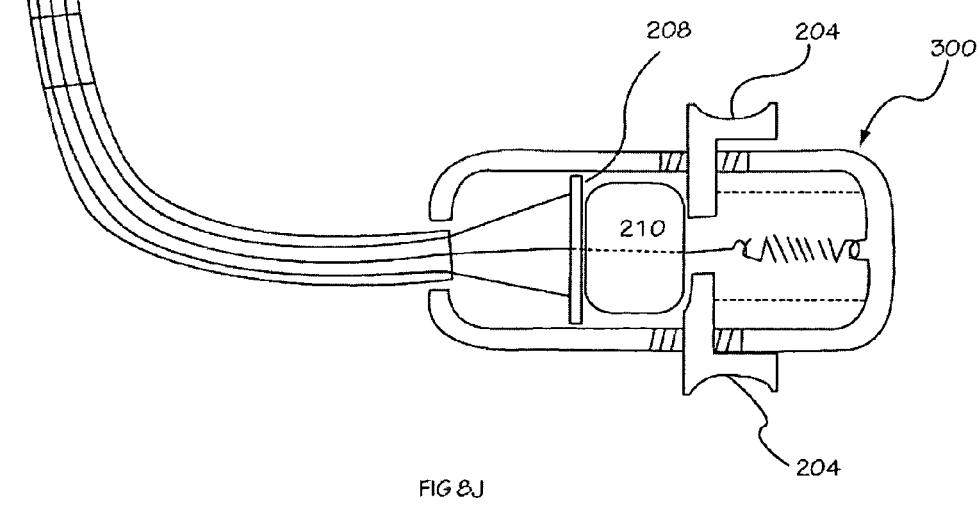

A variation on the plate 208 embodiment also includes a spacer 210 (FIG. 8J). The spacer 210 may be a toroidal shaped compressible balloon, a spring, or other component that provides cushioning and limits the angular rotation of the plate 208 as it is moved axially.

Figure 9:
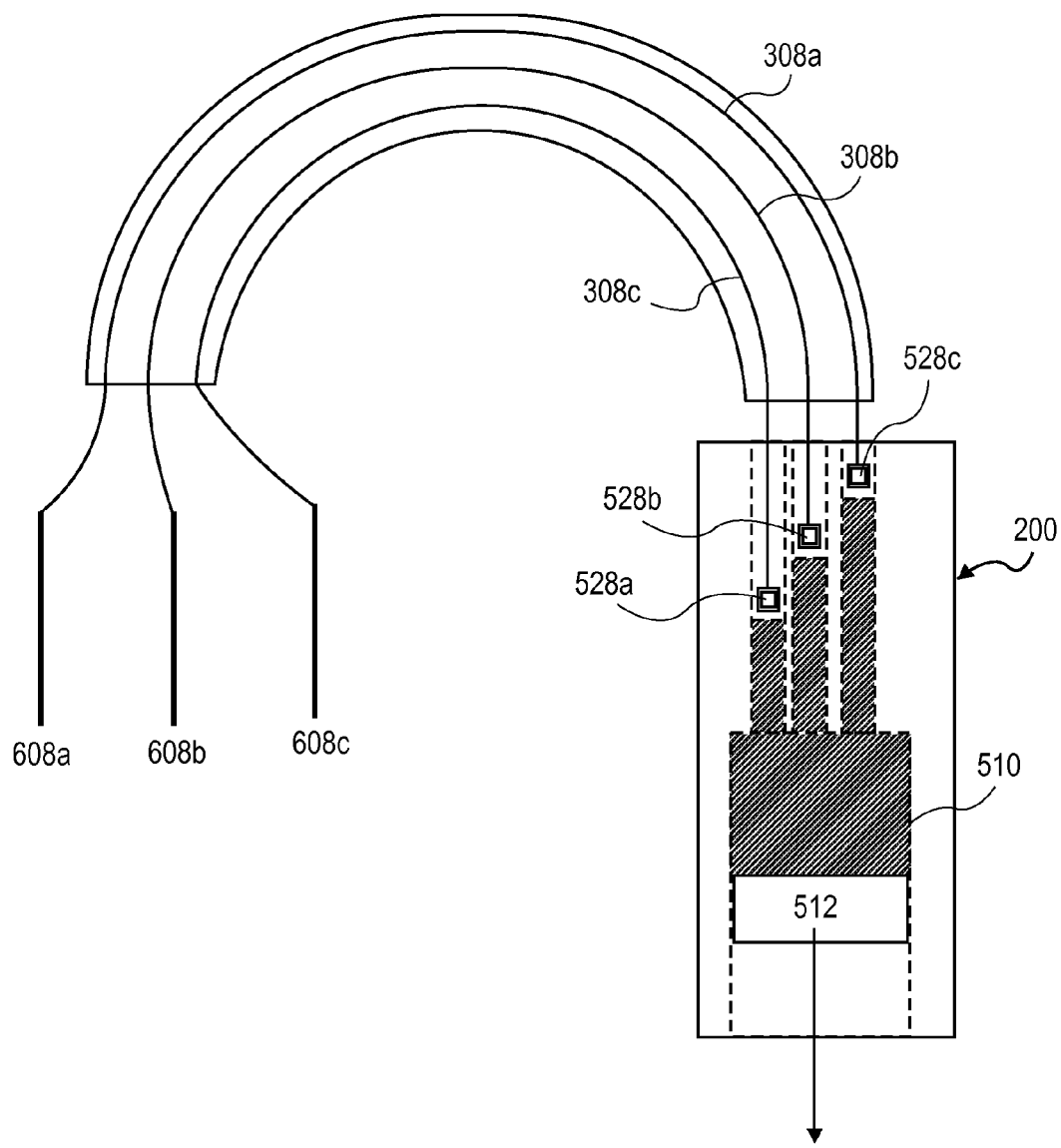
FIG. 9 illustrates a hydraulic compensation mechanism.

Both hydraulic and pneumatic devices may also be used as actuation element compensation devices (FIG. 9). In one embodiment of a hydraulic/pneumatic device there is a fluid manifold 510 contained within the actuation controller 200. The fluid manifold 510 engages a diaphragm or septum 512 that is linked to an actuator 204. As the actuator is manipulated, the diaphragm moves to either withdraw or advance a set of smaller individual plungers 528. The set of smaller individual plunders 528 are linked individually or in groups to actuation elements 308. As the actuator is moved, the fluid causes a corresponding movement in the individual plungers 528, thus imparting force to the deployment mechanism or the implant.

There can be any number of fluidic channels or hydraulic paths linked to solid actuation elements traversing the actuation element paths. As an operator manipulates the individual actuators, the fluid manifold responds by using changes in volumetric capacity to apply pressure to individual actuation elements. In one non-limiting example, the actuator may be a plunger, similar to those used in syringes. As the plunger is advanced or withdrawn, the fluid moves down one or more channels connecting to the individual actuation elements.

Initially the actuation elements may have some slack in them. When the plunger is withdrawn, the response in the pistons connected to the actuation elements may not be the same. Those actuation elements that are slack will be the paths of least resistance in the fluid manifold. Thus the pistons attached to the slack actuation elements will move first, until the actuation elements are roughly all of equal tension. Once all the actuation elements are taut, the actuation elements will interact equally with the deployment mechanism or implant itself. Additional compensation or tension may be incorporated into the fluid manifold 510 or actuator in the event that the actuation element interface sites are designed to respond to differing levels of force.

Figure 10C:
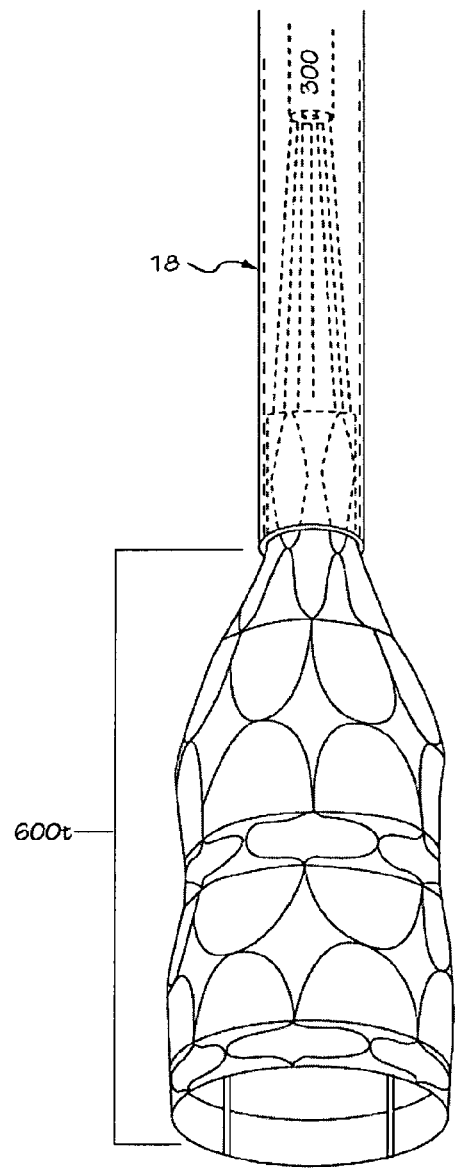
Figure 10D:
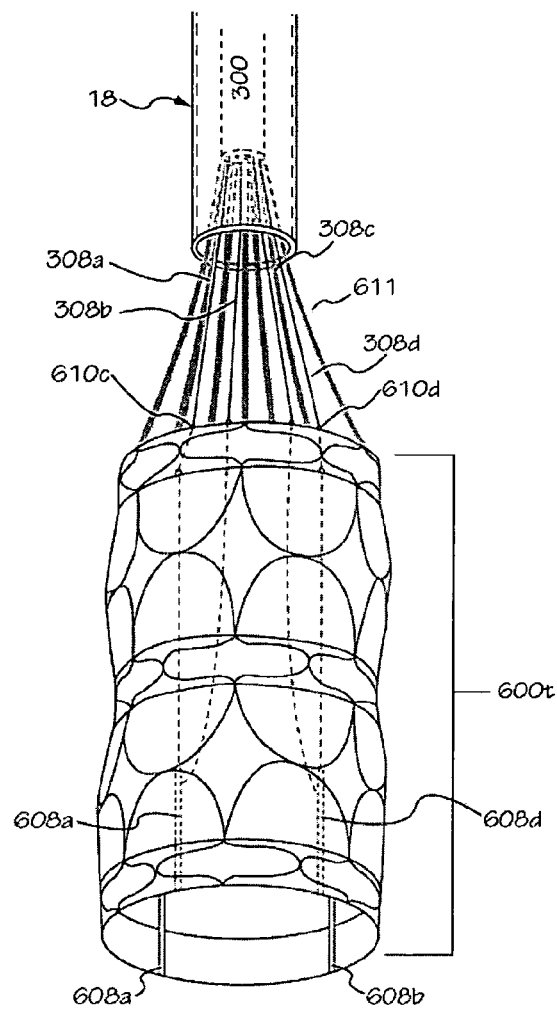
Figure 10E:
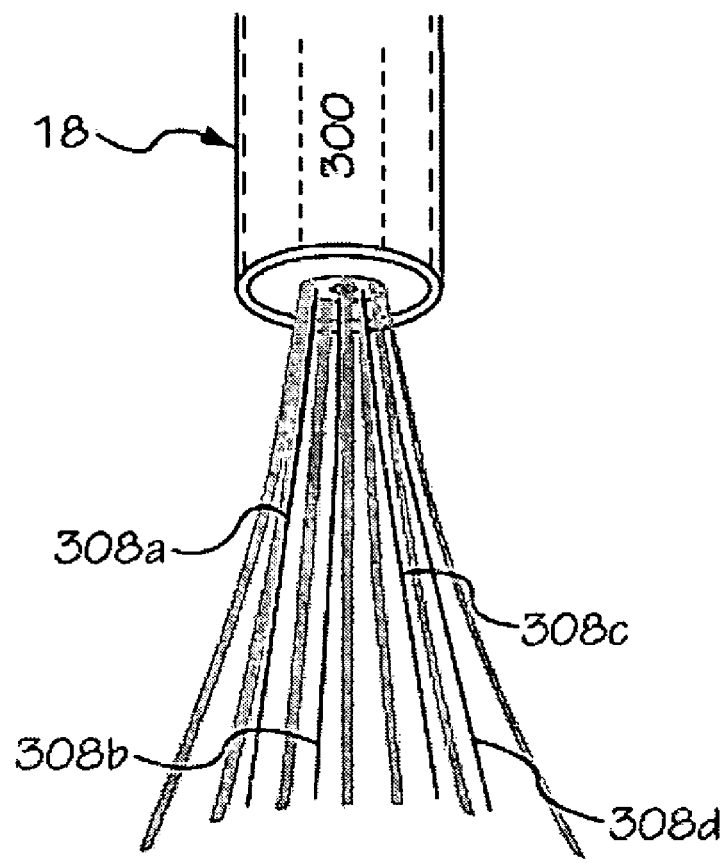
Figure 10E:
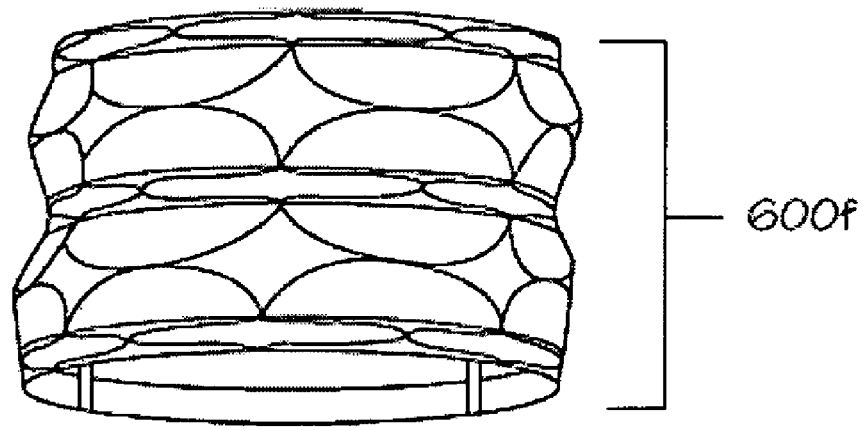

The deployment of the implant is illustrated in FIGS. 10A-E. Initially the implant has a long slender configuration to enable easier positioning of the implant into the patient's vasculature. In its pre-deployment state (FIG. 10A), the implant has a long narrow profile 600i. In this state the implant has its greatest flexibility. Once the deployment tool is positioned properly, the implant can be deployed. Initially the implant is deployed through actuation of the various actuators in the handle or actuation controller. The implant emerges from a tubular constraining sheath 18. This may be achieved by either advancing the implant 602, retracting the sheath 18 by operating the sheath actuator 204s or any combination. As the implant is deployed, it emerges from the constraints of the sheath 18 and expands radially to abut the walls of the native vasculature (not shown). The implant itself may be self expanding and merely constrained by the deployment tool, or it may be of a type that requires active expansion through some additional mechanism. In one example of a replacement heart valve and deployment system, the implant is a combination of a self expanding device and a mechanically actuated expanding device. During deployment the implant is gradually advanced outside the constraining element of the deployment tool such as a sheath (FIG. 10B-D). The implant 602 expands as it is deployed until the entire implant is outside the confines of the sheath 18 or deployment tool 300 (FIG. 10D). The configuration of the implant as a deployed device is fully reversible between the initial state 600*i* (FIG. 10A) and the transitional deployed state 600*t* (FIG. 10D). Furthermore the implant can be completely recovered to return it to its original deployment state as previously illustrated in FIG. 2 and FIG. 3A.

Once the implant 602 is completely out of the sheath 18, the operator can operate one or more of the actuators 308, 611 to foreshorten the implant 602 (FIG. 10D). By operating the actuators 204 on the proximal end, the user causes the actuation elements 308 to impart mechanical force on the implant that lead to the final deployment state 600*f* of the implant 602. A first actuator 204*a* may engage a first actuation element 308*a* to engage post 608*a* of the implant 602. The withdrawing of the actuator 204 can draw actuation element 308*a* proximally to cause the post 608*a* to advance proximally and lead to the engagement of post 608*a* into buckle 610*a*. A series of post and buckle combinations are shown and they may be actuated individually, or as a functional unit using a single actuator. In the case where the posts 608 and buckles 610 are operated as a functional unit, it is desirable that the post and buckles engage simultaneously. Thus, path length compensation is highly desirable among the various actuation element paths. Similarly, other actuation elements 611 extending from a distal end of the deployment tool body 300 can apply a distally directed force on implant 600 at the interface of the actuation elements 611 and implant 600 to assist in the foreshortening of implant 600.

Once the position of the implant is finalized, and the posts and buckles are engaged and locked, the operator can detach the deployment tool 300 from the implant 602. The implant 602 is now in the final deployed state 600*f*. Additional actuators in the actuation controller 200 are used to disengage the actuation elements 308 from the implant and to cause the release of the implant 602 from the distal deployment mechanism.

While it is possible to construct numerous actuators so each individual actuation element may be operated individually, the actuation elements may also be coordinated into functional groups. One actuator may engage the many posts on the implant, while another is used to release the actuation elements from the posts. Another actuator may be linked to the interfaces between the distal mechanical deployment mechanism so as to cause the final release of the implant from the deployment tool. Another logical group may be those mechanical elements needed to deploy the implant outside the sheath, either by advancing the implant forward, withdrawing the sheath or performing both simultaneously. Thus when a multitude of individual actuation elements are grouped together into a logical or functional group, the user may engage one actuator to produce the desired deployment or recapture maneuver.

Connection and operation of the deployment mechanism with the actuation element compensation mechanism is now described in detail (FIG. 11). The implant may be any of a design appropriate for permanent residence in the body, such as that described in U.S. patent application Ser. No. 10/982,388, entitled "Methods and Apparatus for Endovascularly Replacing a Heart Valve" filed on Nov. 5, 2004. The implant 600 itself may have reversibly engaging fasteners such as the posts and buckles previously described. These reversibly engaging fasteners allow the deployment and undeployment of the implant. For example, FIG. 11A shows an alternative post 608 for use in an implantable anchor, such as that shown in FIG. 1B. A proximally directed force applied to post 608 by actuation element 308*a* will move post 608 into engagement with buckle 610 such that element 611 of buckle 610 will move into opening 609 of post 608. A second actuation element 308*b* may be operated to unlock the post and buckle. Variations in path length between these actuation elements and the actuation elements corresponding to other post and buckle pairs may affect the locking and unlocking operations. Likewise, FIG. 11B shows an actuation element 308C adapted to apply a distally-directed force on an expandable anchor 602, such as that shown in FIG. 1A. Proximal movement of unlocking actuation element 308*d* permits the hooked end 309 of actuation element 308*d* to open, thereby releasing the anchor. Once again, variations in path length among multiple actuation elements 308*d* may result in ineffective release of the actuation element 308*c* from the implant, and path length variations among actuation elements 308*c* may result in uneven expansion of the expandable anchor. Other examples of actuation elements are shown in U.S. application Ser. No. 10/982,388.

Thus for the proper deployment of the replacement heart valve, the method utilizes a first step of endovascularly delivering an implant and implant deployment tool or mechanism to an implantation site. The second step is to apply an actuation force to the implant deployment tool or mechanism through actuation elements extending through the patients vasculature while compensating for differences in length between actuation element path lengths to deploy the implant.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. An implant system comprising:
an implant adapted for endovascular delivery and deployment; and
a deployment tool adapted to deploy the implant, the deployment tool comprising:
an actuation controller;
a plurality of actuation elements adapted to apply forces to one or more implant deployment mechanisms comprising an anchor; wherein the anchor has one or more posts attached thereto; wherein the anchor has one or more buckles attached thereto and the implant deployment mechanism is adapted to shift the position of at least one of the one or more posts relative to at least one of the one or more buckles and each actuation element is adapted to extend along an actuation element path within a patient's vasculature; and an actuation element compensation mechanism adapted to compensate for differences in length between the actuation element paths.

2. The system of claim 1 further comprising a catheter, the actuation elements being disposed within the catheter, the actuation element compensation mechanism comprising portions of the actuation element paths extending in a spiral along at least a portion of the catheter.

3. The system of claim 1 wherein the actuation element compensation mechanism comprises a catheter comprising a plurality of actuation element lumens, at least one actuation element being disposed in each of the actuation element lumens.

4. The system of claim 1 wherein the actuation controller comprises the actuation element compensation mechanism.

5. The system of claim 4 wherein the actuation element compensation mechanism comprises a manifold fluid reservoir and a plurality of pistons, each piston being operatively connected to an actuation element and each having a surface exposed to fluid from the reservoir.

6. The system of claim 5 wherein the actuation element compensation mechanism further comprises a source of pressurized fluid communicating with the reservoir.

7. The system of claim 5 wherein the reservoir comprises a movable wall adapted to be moved to change the volume of the reservoir.

8. The system of claim 4 wherein the actuation element compensation mechanism comprises a movable mechanical linkage operatively connected to the actuation elements.

9. The system of claim 8 wherein the mechanical linkage comprises a pivoting element.

10. The system of claim 9 wherein the mechanical linkage comprises two pivoting elements.

11. The system of claim 8 wherein the mechanical linkage comprises a spring at the proximal end of each actuation element.

12. The system of claim 8 wherein the mechanical linkage comprises a pulley.

13. The system of claim 8 wherein the mechanical linkage comprises an actuation element operation mechanism adapted to permit each actuation element to be moved separately and in unison.

14. The system of claim 1 wherein the actuation element compensation mechanism comprises a catheter comprising at least two actuation element lumens, a first actuation element being disposed in a first lumen and a second actuation element being disposed in a second lumen.

15. The system of claim 14 wherein the catheter has a bent shape.

16. The system of claim 14 wherein the first actuation element is shorter than the second actuation element.

17. The system of claim 1 wherein the actuation element compensation mechanism comprises a catheter comprising an actuation element lumen, the actuation elements being disposed in the lumen.

18. The system of claim 17 wherein the actuation element lumen is parallel to and offset from a central axis of the catheter.

19. The system of claim 1 wherein the implant is a replacement heart valve.

20. A method of deploying an implant comprising: endovascularly delivering an implant and implant deployment mechanisms including actuation elements extending through the patient's vasculature along actuation element path lengths to an implant site;

wherein the implant includes an anchor;
wherein the anchor has one or more posts attached thereto;
wherein the anchor has one or more buckles attached thereto;
applying an actuation force to the implant deployment mechanisms through actuation elements extending through the patient's vasculature while compensating for differences in length between actuation element path lengths to deploy the implant; and
wherein applying an actuation force to the implant deployment mechanism shifts the position of at least one of the one or more posts relative to at least one of the one or more buckles.

21. The method of claim 20 wherein the compensating step comprises moving a proximal end of one actuation element proximal to a proximal end of another actuation element.

22. The method of claim 21 wherein the moving step comprises applying fluid pressure to a piston surface operatively connected to each actuation element.

23. The method of claim 21 further comprising locking relative positions of the proximal ends of the actuation elements prior to the applying step.

24. The method of claim 20 wherein the compensating step comprises moving a proximal end of one actuation element distal to a proximal end of another actuation element.

25. The method of claim 24 wherein the moving step comprises applying fluid pressure to a piston surface operatively connected to each actuation element.

26. The method of claim 24 further comprising locking relative positions of the proximal ends of the actuation elements prior to the applying step.

27. The method of claim 20 wherein the applying step comprises moving a hinged mechanical linkage to which proximal ends of the actuation elements are operatively connected.

28. The method of claim 20 wherein the applying step comprises moving a mechanical linkage operatively connected to proximal ends of the actuation elements through a pulley.

29. The method of claim 20 wherein the applying step comprises moving a mechanical linkage operatively connected to proximal ends of the actuation elements through springs.

30. The method of claim 20 wherein the implant is a replacement heart valve.

31. The method of claim 20 wherein the applying step comprises applying an actuation force to the implant through the implant deployment mechanisms to deploy the implant.

32. The method of claim 20 wherein the applying step comprises applying an actuation force to the implant through the implant deployment mechanisms to foreshorten the implant.

33. A method for delivering an implant, the method comprising:
providing an implant, the implant comprising:
an anchor,
a post attached to the anchor,
an actuation element coupled to the post, and
a buckle attached to the anchor;
wherein the implant is configured to shift between a delivery configuration and a deployed configuration;
advancing the implant through the vasculature of a patient to a position adjacent to an area of interest;

applying an actuation force to the actuation element;
wherein applying an actuation force to the actuation element draws the post into the buckle and shifts the implant from the delivery configuration to the deployed configuration;
wherein the implant includes one or more additional actuation elements; and
wherein an actuation element compensation mechanism is associated with the actuation element and the one or more additional actuation elements.

34. The method of claim 33, wherein the implant further comprises one or more additional posts and one or more additional buckles corresponding to the one or more additional posts.

35. The method of claim 34, further comprising applying an actuation force to the one or more additional actuation elements to draw the one or more additional posts into the corresponding one or more additional buckles.

36. The method of claim 33, wherein the actuation element compensation mechanism includes a winding actuation element path.

37. The method of claim 33, wherein the actuation element compensation mechanism includes a pulley and one or more tackles.

38. The method of claim 33, wherein the implant includes a heart valve attached to the anchor.

* * * * *